US006187991B1

(12) United States Patent
Soeller et al.

(10) Patent No.: US 6,187,991 B1
(45) Date of Patent: *Feb. 13, 2001

(54) TRANSGENIC ANIMAL MODELS FOR TYPE II DIABETES MELLITUS

(75) Inventors: Walter C. Soeller, Mystic; Maynard D. Carty, Gales Ferry; David K. Kreutter, Madison, all of CT (US)

(73) Assignee: Pfizer Inc, New York, NY (US)

( * ) Notice: Under 35 U.S.C. 154(b), the term of this patent shall be extended for 0 days.

This patent is subject to a terminal disclaimer.

(21) Appl. No.: 08/446,935

(22) Filed: May 23, 1995

(51) Int. Cl.[7] ............................. C12N 15/00; A61K 48/00
(52) U.S. Cl. ..................... 800/2; 435/320.1; 435/172.3
(58) Field of Search ............................. 800/2; 435/320.1, 435/240.2, 172.3

(56) References Cited

U.S. PATENT DOCUMENTS

| 4,736,866 | 4/1988 | Leder et al. | 800/2 |
| 5,175,383 | 12/1992 | Leder et al. | 800/2 |
| 5,175,384 | 12/1992 | Krimpenfort et al. | 800/2 |
| 5,221,778 | 6/1993 | Byrne et al. | 800/2 |
| 5,387,742 | 2/1995 | Cordell | 800/2 |

FOREIGN PATENT DOCUMENTS

| WO9314200 | 7/1993 | (WO) . |
| WO9400558 | 1/1994 | (WO) . |

OTHER PUBLICATIONS

Venchere et al., "Transgenic Mice Overproducing Islet Amyloid Polypeptide Have Increased Insulin Storage and Secretion In Vitro"; *Diabetologia*, (1994) 37: pp. 725 –728.

Fox et al., Human Islet Amyloid Polypeptide Transgenic Mice As A Model Of Non–Insulin–Dependent Diabetes Mellitus (NIDDM); FEBS, vol. 323, No. 1.2, pp. 40 –44, May, 1993.

Hoppener et al., "Molecular Physiology Of The Islet Amyloid Polypeptide (IAPP)/Amylin Gene in Man, Rate, And Transgenic Mice"; *J. of Cellular Biochemistry*, 55S: pp. 39–53 (1994).

Hoppener et al., "Chronic Overproduction Of Islet Amyloid Polypeptide/Amylin In Transgenic Mice: Lysosomal Localization of Human Islet Amyloid Polypeptide And Lack of Marked Hydperglycaemia Or Hyperinsulinaemia"; *Diabetologia*, (1993) 36: pp. 1258 –1265.

de Koning et al., "Human Islet Amyloid Polypeptide Accumulates At Similar Sites In Islets Of Transgenic Mice and Humans"; *Diabetes*, vol. 43, pp. 640 –644, May, 1994.

de Koning, "Intra— and Extracellular Amyloid Fibrils Are Formed In Cultured Pancreatic Islets of Transgenic Mice Expressing Human islet Amyloid Polypeptide"; *PNAS*, vol. 91, pp. 8467 –8471, Aug., 1994.

Johnson et al., Islet Amyloid, Islet–Amyloid Polypeptide, And Diabetes Mellitus, *NEJM*, vol. 321, No. 8, pp. 513 –518, (1989).

Kappel et al. "Regulating gene expression in transgenic animals, " Current Opinion in Biotechnology, vol. 3: 548–553, 1992.*

Hoppener et al. "IAPP/amylin transgenic mice as an in vivo model system for type–2 diabetes mellitus?" Biochemical Society Transactions, vol. 21 (1): 28S, Feb. 1993.*

Hoppener et al. "The role of islet amyloid polypeptide (IAPP)–amylin in the pathogenesis of type–2 diabetes mellitus: Implications from a trangenic mouse study" 3rd European Congress of Endocrinology, European Journal of Endocrinology, vol. 130 (Supp. 2, Jul. 1994.*

* cited by examiner

*Primary Examiner*—Jasemine C. Chambers
*Assistant Examiner*—Karen M. Hauda
(74) *Attorney, Agent, or Firm*—Peter C. Richardson; Gregg C. Benson; Robert F. Sheyka

(57) ABSTRACT

The generation of transgenic animal models for testing various treatments of Type II Diabetes Mellitus are described. The DNA construct allows pancreatic β cell-specific expression of human islet associated polypeptide (IAPP) under the regulation of the rat insulin II promoter in both cell lines and transgenic animals. The DNA construct is introduced into animal embryos by microinjection as one or multiple copies or into established cell lines by electroporation. The transgenic animals develop amyloid plaque deposits in the islets of Langerhans in the pancreas, fasting hyperglycemia, glycouria and diabetic glomerulosclerosis at 3 to 5 months of age. The cell lines can be screened for treatments that inhibit expression of human IAPP; the transgenic animals can be screened for treatments that either enhance or inhibit the progression of this disease phenotype.

3 Claims, 10 Drawing Sheets

TRANSGENIC ANIMAL MODELS FOR TYPE II DIABETES MELLITUS

BACKGROUND OF THE INVENTION

This invention relates to a process for genetic alteration of mammalian cell lines and animals such that they express the protein encoded by the human Islet Amyloid Polypeptide (IAPP) gene. IAPP, formerly known as amylin, is the major protein component of pancreatic islet amyloid that forms in the pancreata of Non-insulin Dependent Diabetes Mellitus (NIDDM) patients. Recent studies of IAPP structural and functional characteristics suggest that IAPP, along with insulin and other hormones, plays a major role in carbohydrate metabolism. IAPP is produced, stored and secreted by pancreatic β cells in the islets of Langerhans. It can mimic the phenomenon of insulin resistance seen in NIDDM by inhibiting glucose uptake and glycogen synthesis in muscle, and liver tissue. The generation of amyloid deposits in humans is thought to be due to the ability of the center portion of the peptide (amino acids 20–29) to form a β pleated sheet structure, Rodent IAPP differs from human IAPP in that the sequences in this otherwise highly conserved protein between amino acids 20–29 are not conserved and amyloid deposits do not form in rodent pancreata. A working hypothesis is that overexpression of human IAPP leads to insulin resistance in peripheral tissues and in the formation of amyloid deposits.

Transgenic animals, especially mice, have proven to be very useful in dissecting complex systems to generate new information about human disease. Selective expression of human genes in such mice has generated novel model systems to study disease, especially when overexpression of a gene results in a disease state. With such transgenic mice, one can address issues concerning (1) tissue specificity of expression; (2) testing of hypotheses that overexpression of a particular gene leads to disease; (3) the number and identity of tissues/organs that are affected by this overexpression; and (4) effects of various treatments, including drugs, on the progression or amelioration of the disease phenotype.

The generation of transgenic mice that express human IAPP has been reported in the literature, though none of these animals developed a diabetic phenotype. Niles Fox et al. (FEBS Letters 323, 40–44 [1993]) constructed a transgene that fused the rat insulin promoter sequence to a genomic DNA fragment containing the entire human IAPP gene (exons 1–3 and introns 1 and 2). Transgene RNA expression was detected in pancreas, anterior pituitary and brain. Although plasma IAPP levels were 5-fold elevated relative to nontransgenic littermates, no metabolic consequence of this elevation was observed. C. B. Verchere et al. (Diabetologia 37, 725–729 [1994]) used a 600 bp fragment encoding the entire human proIAPP sequence. Their transgenic animals exhibited greater pancreatic content of both IAPP and insulin relative to nontransgenic littermate controls. Increased secretion of both hormones was also detected in perfused pancreas studies. No clinical manifestations of this enhanced storage and secretion were observed. Hoppener et. al. (Diabetologia 36, 1258–1265 [1993]) described the generation of multiple transgenic lines that expressed either human or rat IAPP in the mouse endocrine pancreas. Höppener's group used a 703 bp rat insulin II promoter fragment to drive expression of human or rat IAPP from genomic DNA fragments. Plasma IAPP levels were up to 15 fold elevated but no hyperglycemia nor hyperinsulinemia were observed. In a subsequent study, no amyloid plaque was seen to accumulate in vivo but intra- and extracellular amyliod fibrils did form when islets from these transgenics were cultured in vitro under conditions mimicking hyperglycemia (De Koning et al. Proc. Natl. Acad. Sci. 91, 8467–8471 [1994]).

SUMMARY OF THE INVENTION

In one embodiment, the present invention is directed to recombinant DNA comprising a non-IAPP promoter, a sequence encoding human IAPP or an active fragment thereof functionally linked to a human albumin intron I encoding sequence, a human GAPDH termination encoding sequence and a human GAPDH polyadenylaton encoding sequence, said DNA resulting in expression of a diabetic phenotype when incorporated into a suitable host.

Especially preferred is recombinant DNA wherein the non-IAPP promoter is selected from the group consisting of promoters for the genes for rat insulin I, rat insulin II, human insulin, mouse IAPP, rat beta cell-specific gluocokinase, glucose transporter 2, human tyrosine amino transferase, human albumin, mouse albumin, rat liver specific glucokinase, and mouse metallothionein.

Also preferred is recombinant DNA wherein said promoter is the rat insulin II promoter.

Especially also preferred is recombinant DNA wherein said sequence encoding human IAPP or an active fragment thereof has the characteristics of cDNA.

Further preferred is recombinant DNA wherein said sequence encoding human IAPP or an active fragment thereof has the characteristics of genomic DNA.

Also further preferred is recombinant DNA wherein said sequence is that of SEQ ID NO: 4.

Also especially further preferred is recombinant DNA wherein said sequence of cDNA is that of SEQ ID NO: 5.

In another embodiment, the DNA sequence encoding human IAPP is replaced by a DNA sequence encoding mouse IAPP or an active fragment thereof, with said mouse DNA preferably having the characteristics of cDNA.

The present invention is also directed to vectors comprising recombinant DNA of the present invention (SEQ. ID NO: 1).

The present invention is also directed to an eukaryotic cell line comprising recombinant DNA of the present invention with preferred cell lines selected from the group consisting of rat insulinoma (RIN) cells, hamster insulinoma (HIT) cells and β-TC3 mouse insulinoma cells.

The present invention is also directed to transgenic non-human mammals comprising recombinant DNA of the present invention with especially preferred transgenic mammals being mice and rats, said transgenic mammals exhibiting a diabetic phenotype.

In another embodiment, the present invention is directed to a method for treating an animal having disease characterized by an over expression of an IAPP gene product comprising,
  administering a therapeutically-effective amount of an inhibitor of the over expression of said IAPP gene product to said mammal.

In yet another embodiment, the present invention is directed to a method of evaluating the effect of a treatment comprising administering said treatment and evaluating the effect of said treatment on the product of over expression of a gene encoding IAPP.

Preferred is the method wherein said treatment is administered to an animal with an especially preferred animal being a human.

The present invention is also directed to a method for determining if a subject is at risk for diabetes or obesity comprising examining said subject for the over expression of an IAPP gene product, said over expression being indicative of risk.

In still yet another embodiment, the present invention is directed to a method of evaluating an animal model for a disorder or disease state comprising determining if an IAPP gene in said animal model is expressed at a predetermined level with a preferred method being wherein said level is higher than the level in a wild type or normal animal.

DETAILED DESCRIPTION OF THE INVENTION

The Plasmids:

Plasmid pRIPHAT I(rat insulin promoter human IAPP transgene) (SEQ. ID NO: 1) contains DNA fragments from 5 different sources, three from human genes, the fourth from rat and the fifth being a commercially available plasmid vector. They are the rat insulin II promoter ( 876 bp); (SEQ ID NO: 2) human IAPP coding sequence (278 bp) (SEQ ID NO: 3), human albumin intron I( 720 bp) (SEQ ID NO: 4), and the human glyceraldehyde-3-phosphate dehydrogenase (GAPDH) gene's polyadenylation site and RNA termination region (546 bp) (SEQ ID NO: 5). The commercially available plasmid is Bluescript SK(−) (Stratagene, La Jolla, Calif.) (SEQ. ID NO: 6). Enzymatic manipulations of recombinant DNA, including ligations, restriction endonuclease digestions, DNA synthesis reactions, and transformations of *E. coli* were carried out according to well-established procedures as described in Sambrook, J., Fritsch, E. F. and Maniatis, T. Molecular Cloning: A Laboratory Manual. 2nd Ed. Cold Spring Harbor Laboratory Press, New York, 1989.

Figure 1A:
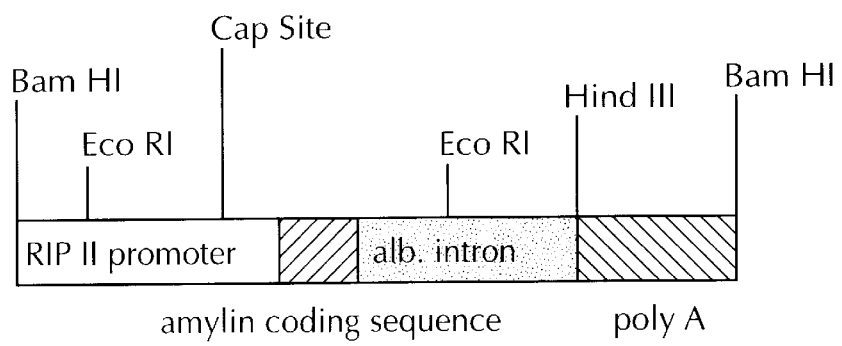
FIG. 1a is a linear map of the RIPHAT transgene. The human IAPP cDNA sequence is depicted in black; the rat insulin II promoter is depicted as a white box, the human albumin intron is a darkly shaded box, the human GAPDH polyadenylation region (labeled poly A) is depicted as a lightly shaded box.
Figure 2:
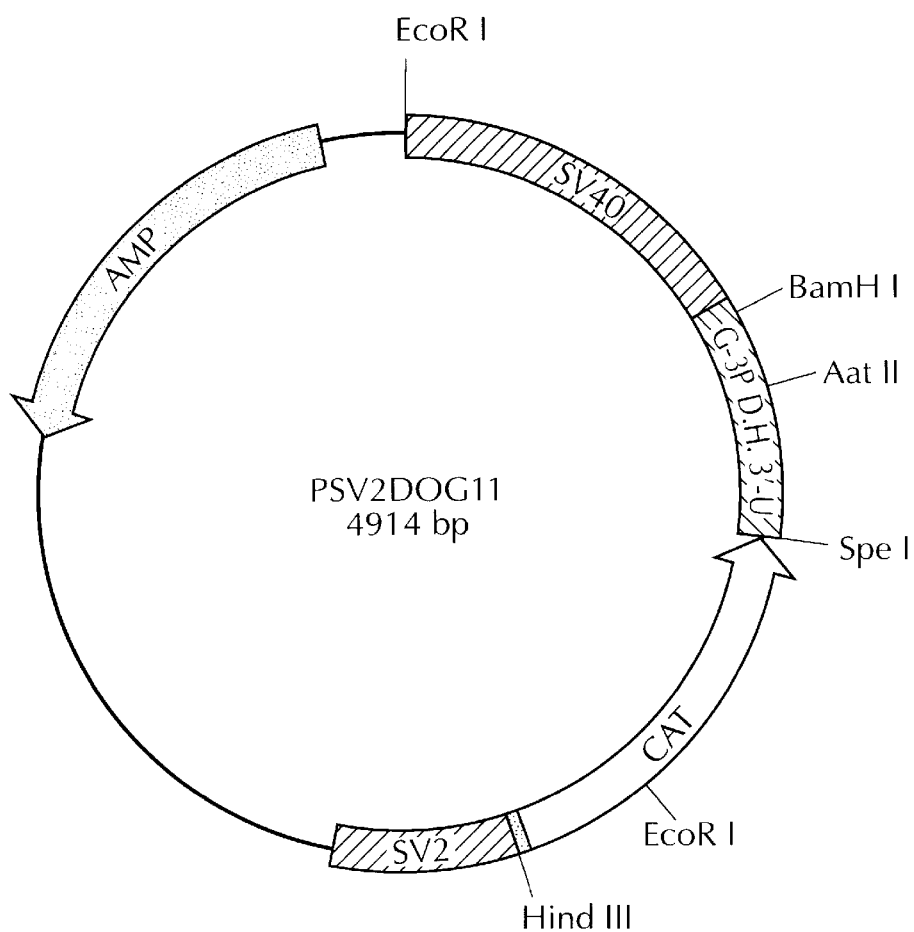
FIG. 2 is a circular map of the plasmid pSV2Dog1. pSVDog1 was constructed by inserting the PCR-modified CAT gene (BspM I/BamH I fragment) downstream of the SV40 promoter (BamH I/Nco I partial fragment from pLuxF3). The resulting plasmid contains the CAT gene coding sequence fused at its 5' end with optimal mammalian translation sequences, and fused at its 3' end with the firefly luciferase 3'-untranslated region and poly A addition site. Expression of the modified CAT gene is driven by the SV40 promoter.

The human albumin intron I (SEQ ID NO: 4) and GAPDH gene fragments (SEQ ID NO: 5) were obtained from the plasmid pSV2Dog15 by digestion of this plasmid with Bam HI and ApaLI and isolation of the 1262 bp fragment containing these two regions. pSV2Dog15 was constructed by David Lloyd and John Thompson of Pfizer, Inc. They generated the human albumin intron I sequence by polymerase chain reaction (PCR) amplification(Innis, M. A. et al. eds., PCR Protocols, Academic Press, New York 1990) of this portion of the albumin gene using human genomic DNA(obtained from Clontech, Palo Alto, Calif.) and DNA oligomers 18505.022 (sequence 5' CCCTCTAGAAGCT-TGTCTGGGCAAGGGAAGAAAA 3') (SEQ ID NO: 8) and 18505.024 (sequence 5' GGGAAGCTTCTA-GACTTTCGTCGAGGTGCACGTAAAA 3') (SEQ ID NO: 9). Since these oligomers included exogenous Xba I sites on their ends, the resulting PCR product was digested with Xba I and inserted into the compatible Spe I site in pSV2Dog 11. This plasmid, constructed by David Lloyd, in turn already contained the human GAPDH polyadenylation region. It was also generated by PCR cloning using human genomic DNA as the template and oligomers 18970.246 (sequence 5' CAAACCGGATCCGCCCTGACTTCCTC-CACCTGTCAGC 3') (SEQ ID NO: 10) and 18970.244 (sequence 5' CACAACACTAGTGACCCCTGGACCAC-CAGCCCCAGC 3') (SEQ ID NO: 11) as the PCR primers. The PCR product generated in this manner was digested with Spe I and Bam HI and inserted into SpeI/Bam HI digested pSV2Dog1 (see FIG. 2).

The 1262 bp, Apa LI/Bam HI albumin intronl-GAPDH polyA region hybrid fragment was ligated to a 278 bp PCR-amplified DNA fragment containing the coding region for the preproIAPP protein product. This fragment was amplified by using an IAPP cDNA (lambda phage DNA hIAPP-c1, obtained from Sietse Mosselman, Rijksuniversiteit te Utrecht, The Netherlands and described in Mosselman, S. et al., Febs Lett. 247, 154–158 [1989]) as the template and oligomers 19383.288 (sequence 5'GTCATGT-GCACCTAAAGGGGCAAGTAATTCA 3') (SEQ ID NO: 12) and 19987.116 (sequence 5' GAAGCCATGGGCATC-CTGAAGCTGCAAGTA 3') (SEQ ID NO: 13) as the PCR primers. The resulting 1523 bp fragment was ligated to pSuperLuc (pSL) to generate plasmid pSLA10. pSL is a DNA plasmid containing the luciferase reporter gene (Mosselman, S. et al. FEBS Lett. 271, 33–36 [1990]). In this case, the plasmid was used only for the presence of convenient Nco I and Bam HI restriction sites.

Figure 3A:
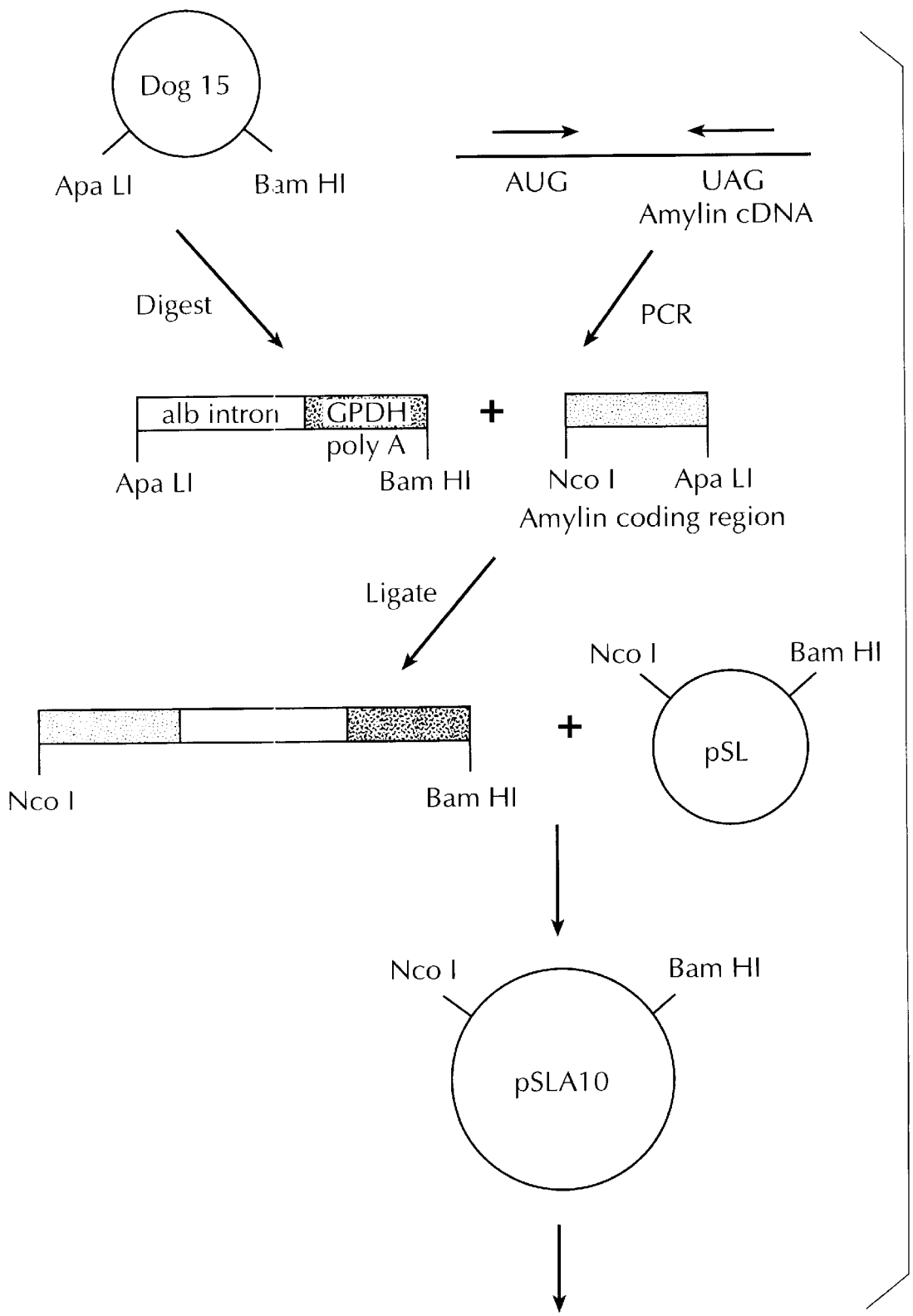
FIG. 3A is a circular map of the plasmid pSV2Dog11 containing the human glyceraldehyde 3 phosphate dehydrogenase polyadenylation region used to construct the plasmid pDog 15. pSV2Dog11 was constructed by inserting the PCR amplified human glyceraldehyde-3-phosphate dehydrogenase 3'-untranslated region into Spe I/BamH I digested pSV2Dog1. This places GAPDH 3' non-coding sequences downstream of the CAT coding region.
Figure 3B:
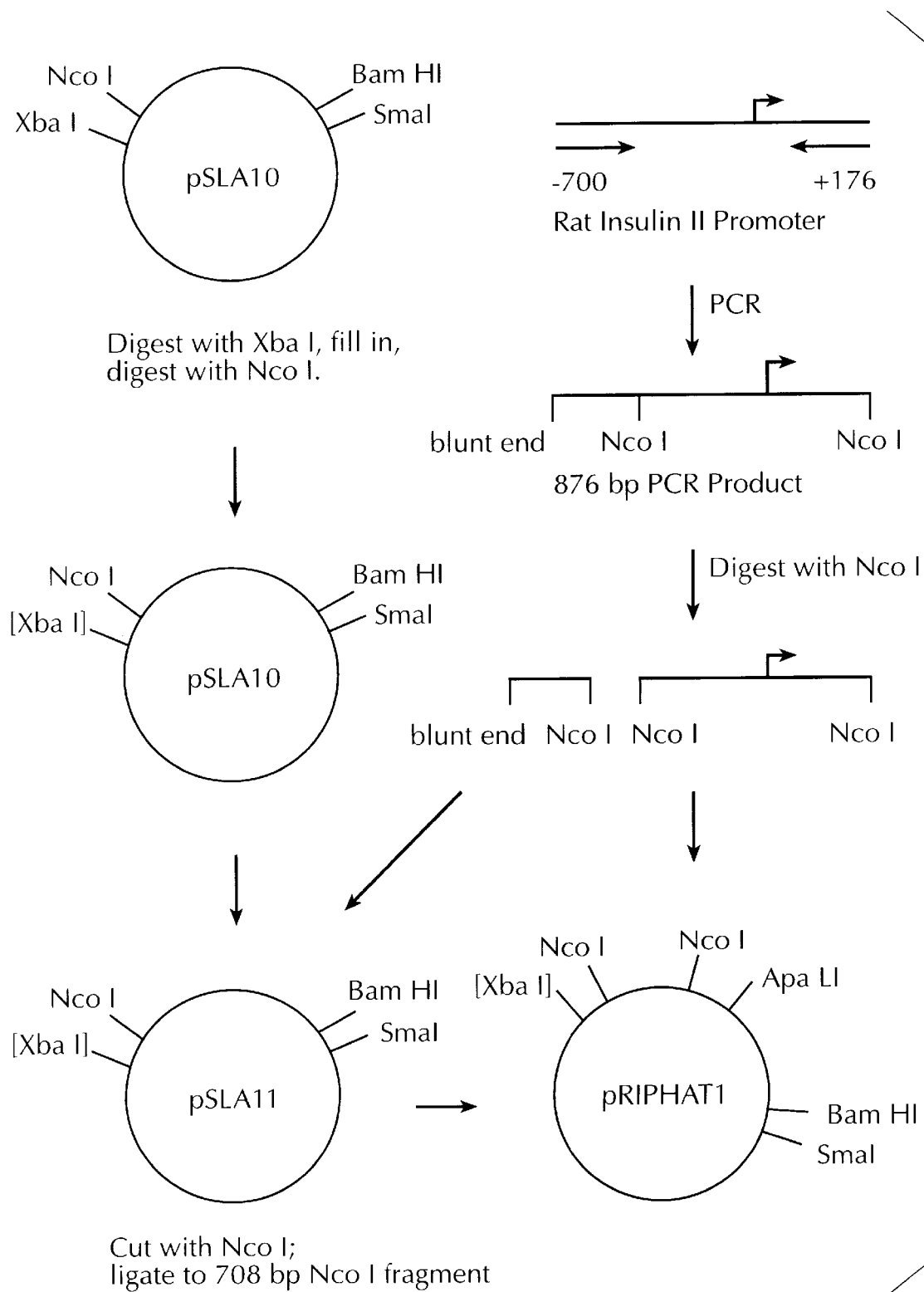
FIG. 3B is a schematic drawing of the cloning strategy used to construct pRIPHAT1, starting with plasmid pDog15.
Figure 4:
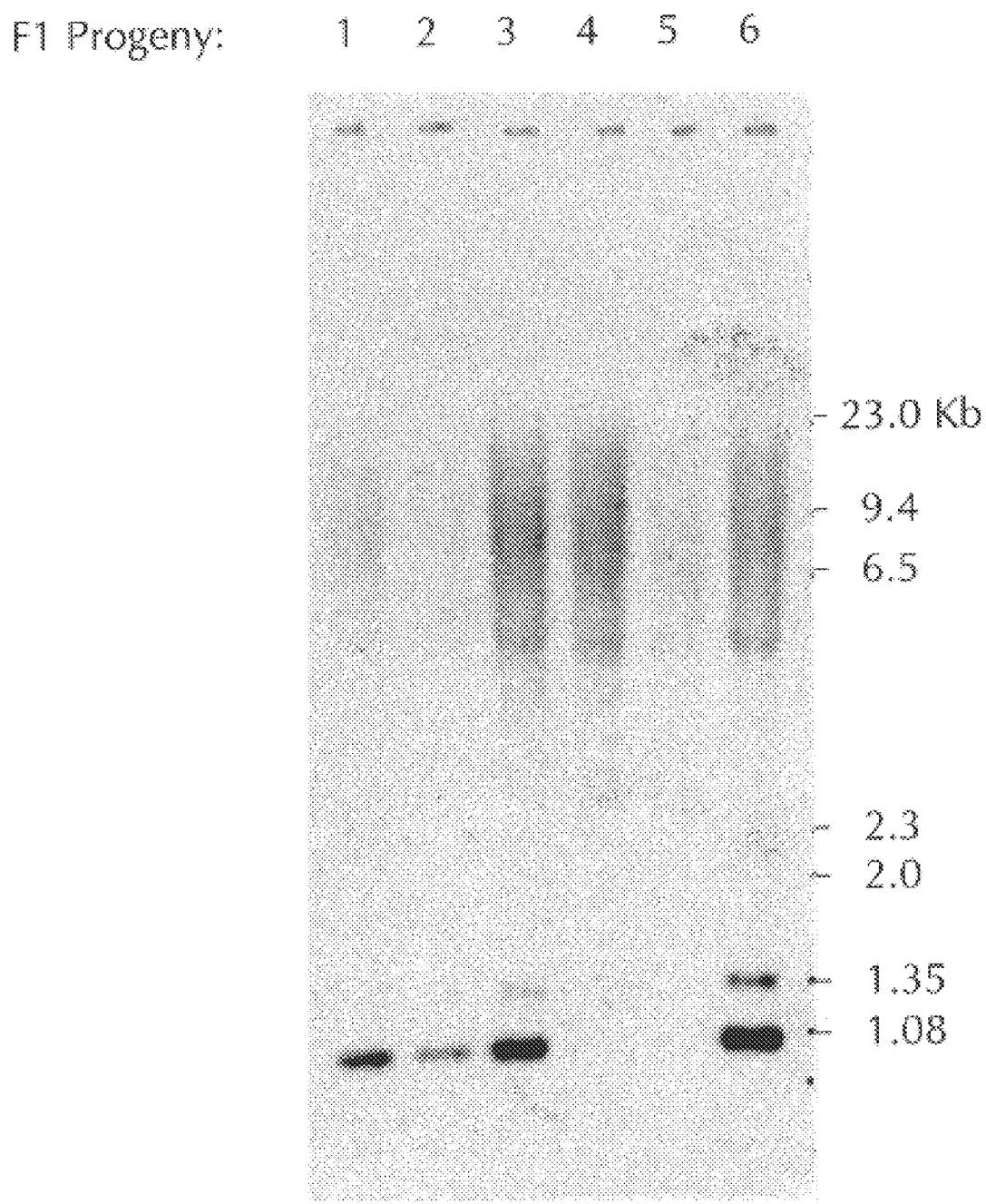
FIG. 4 is an autoradiogram of a genomic DNA southern blot of 6 tail DNAs digested with the restriction endonuclease EcoRI and hybridized to the $^{32}$P-labelled human GAPDH fragment within the RIPHAT transgene DNA. The 6 lanes represent a litter of animals produced from a cross of RIPHAT transgenic line RG male and FVB/N wild type female.
Figure 5:
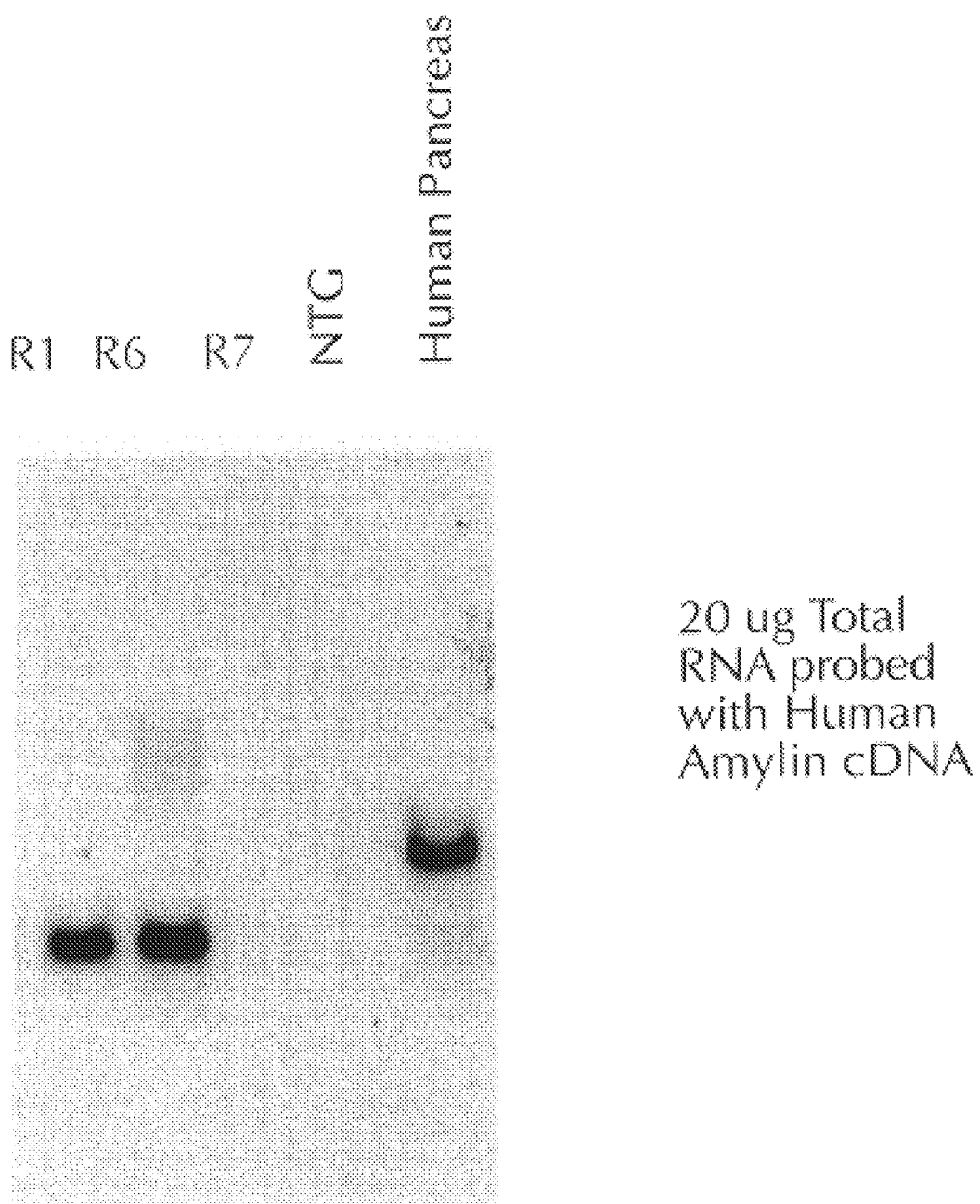
FIG. 5 is an autoradiogram of a northern blot of total pancreatic RNA isolated from the transgenic lines RHA, RHF and RHG in addition to pancreatic RNA from Human Pancreas and a nontransgenic mouse. The blot was hybridized to a human IAPP cDNA fragment labelled with [alpha $^{32}$P]dCTP.
Figure 6:
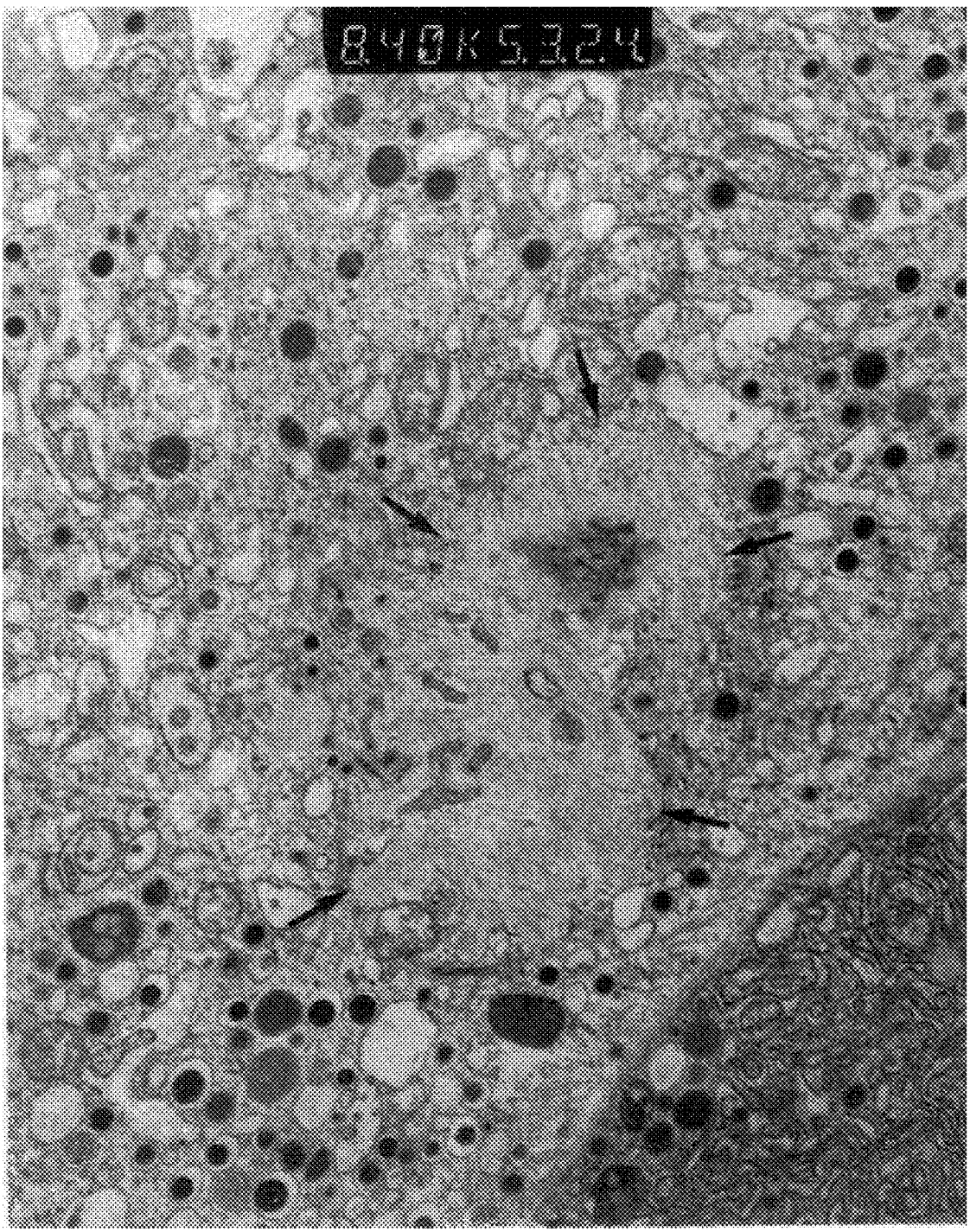
FIG. 6 is an electron micrograph of a pancreatic β cell. The arrows outline an intracellular amyloid plaque deposit.
Figure 7:
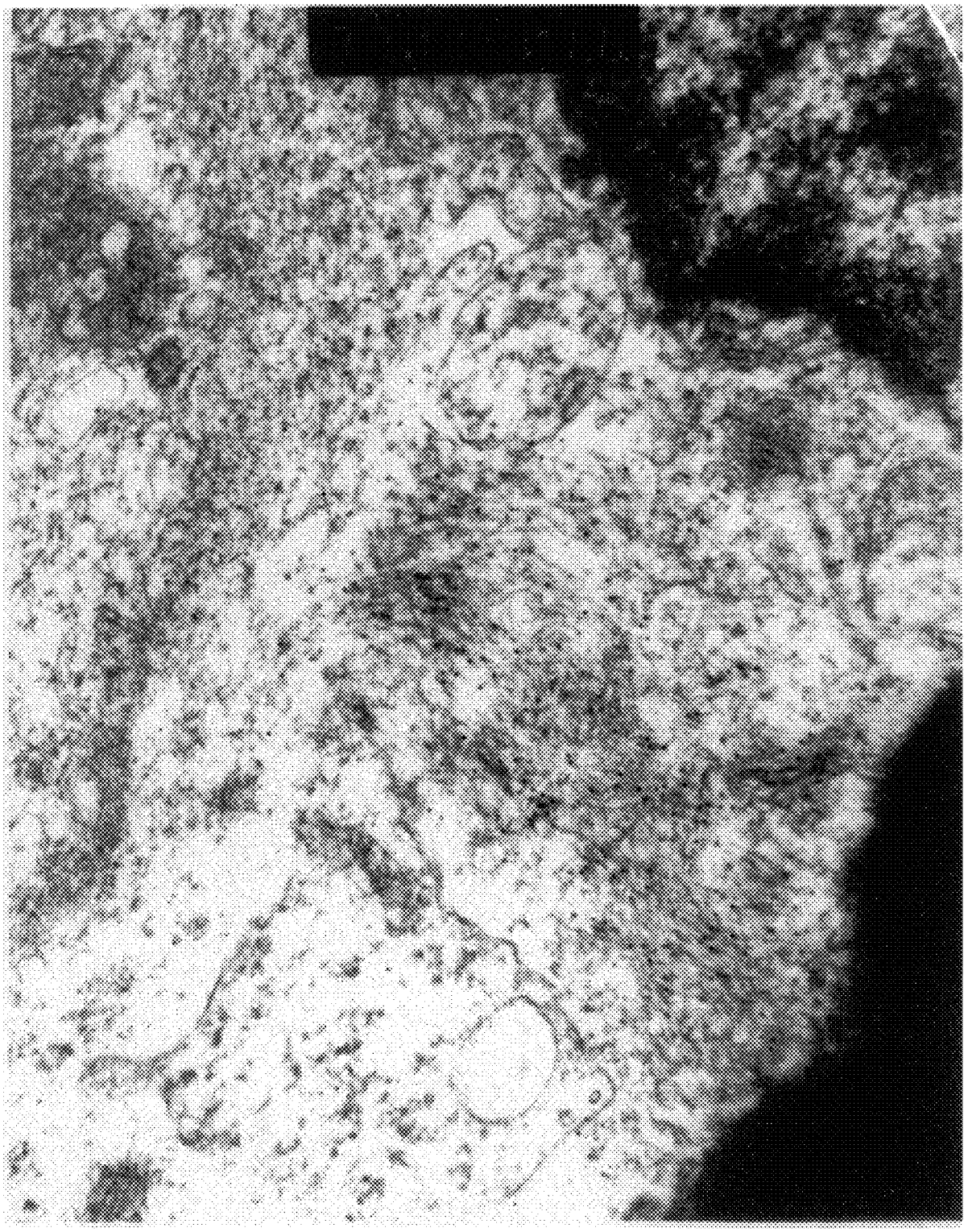
FIG. 7 is an electron micrograph showing a 37,000 fold magnification of immunogold staining of intracellular amyloid plaque by means of a rabbit anti human IAPP antibody.
Figure 8:
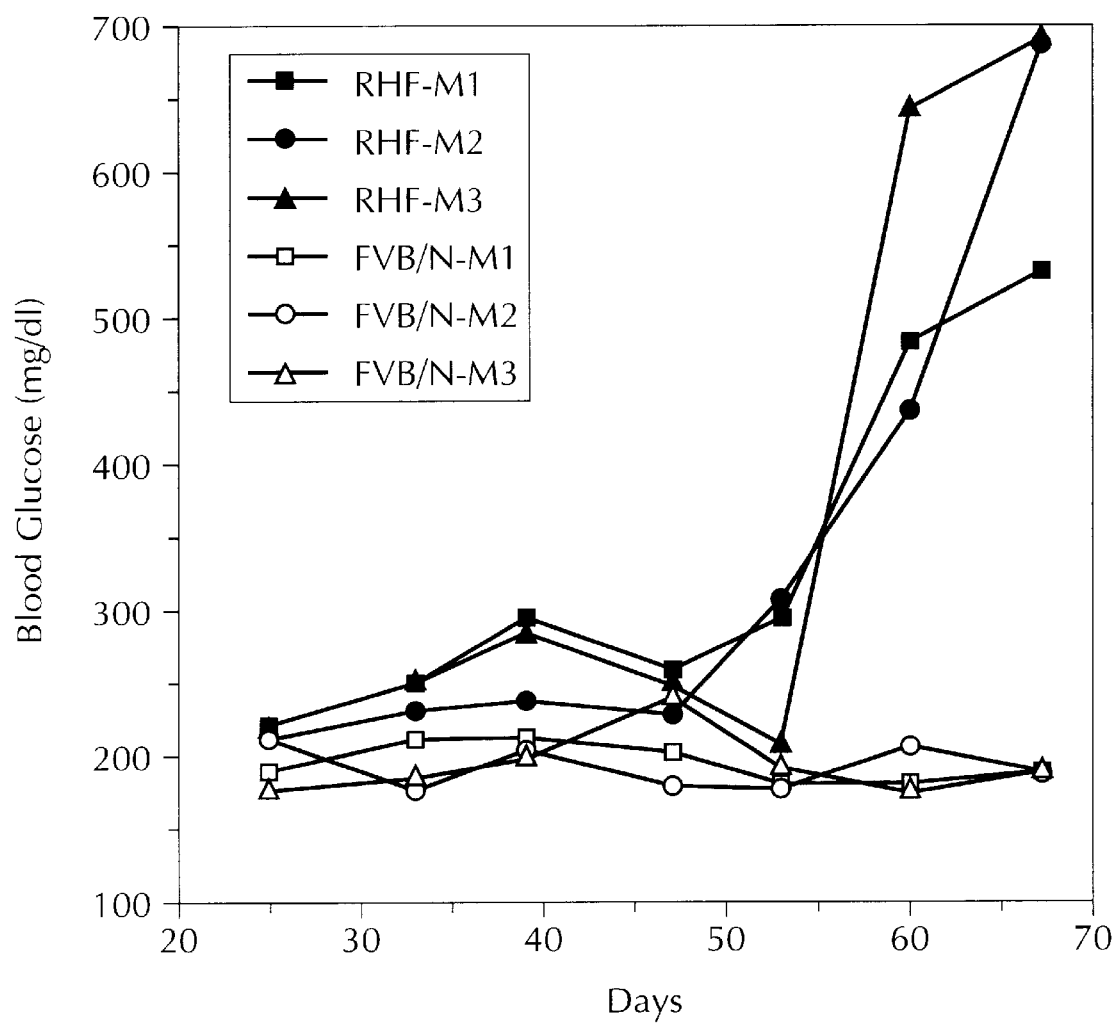
FIG. 8 is a graphical representation of the appearance of hyperglycemia in 3 male RHF homozygous mice compared to 3 nontransgenic (FVB/N strain) male mice.
Figure 9A:
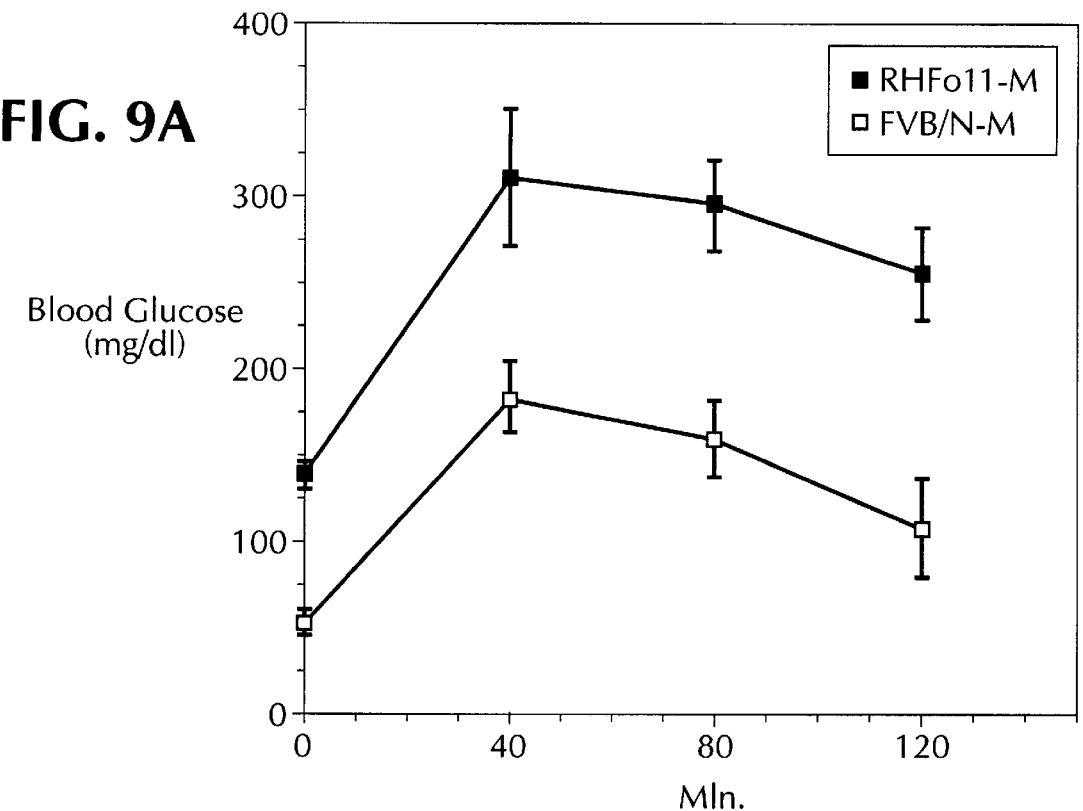
FIG. 9 depicts the results of an oral glucose tolerance test performed on 5 week old RHF homozyous transgenic males (litter # RHF11, n=5) and females (litter # RHF11, n=3) compared to age-matched nontransgenic FVB/N mice.
Figure 9B:
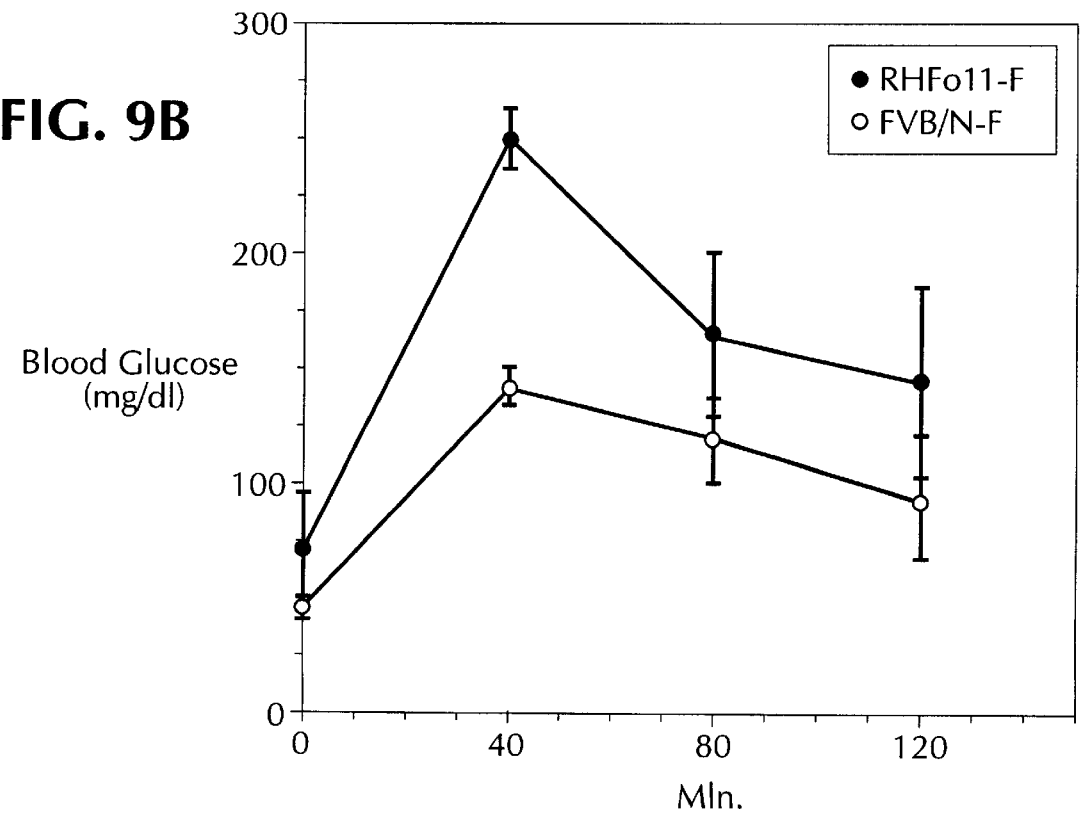

The rat insulin II promoter (SEQ ID NO: 2) and 5' untranslated leader region were generated by PCR amplification of rat genomic DNA (obtained from Clontech, cat # 6750-1) using oligomers 19383.284 ( sequence 5' GTCAGGAATTCGGATCCCCCAACCACTCCAA-GT 3') (SEQ ID NO: 14) and 19383.292 (sequence 5' ACAGGGCCATGGTGGAACAATGA-CCTGGAAGATA 3') (SEQ ID NO: 15). The oligomer 19383.292 contains a point mutation; and was so designed to introduce an Nco I site at the 3' end of the fragment by altering one nucleotide (A to C) 2 residues 5' of the initiation codon. The 883 bp PCR product was cleaved with Nco I to generate a 175 bp blunt end/Nco I fragment and a 708 bp fragment with 2 Nco I ends. The plasmid pSLA 10 was digested with Xba I. The resulting 5' overhangs were filled in with Klenow polymerase and dNTPs to generate blunt ends. The plasmid was subsequently digested with Nco I and ligated to the 175 bp blunt end/Nco I rat insulin II fragment to generate pSLA11 (see FIG. 3).

pSLA11 was digested with Nco I and ligated to the 708 bp Nco I rat insulin II fragment to generate plasmid pSLA12. Proper orientation of the 708 bp Nco I fragment was confirmed by digestion of the plasmid with Eco RI and Bam HI. The chimeric transgene (rat insulin II promoter and 5' untranslated leader, IAPP coding region, albumin intron I, GAPDH polyadenylation region) (SEQ ID NO: 7) was transferred from the pSL backbone to Bam HI-linearized Bluescript SK(−) by partial Bam HI digestion of pSLA12 to generate pRIPHAT I (SEQ ID NO: 1). The rat insulin II promoter and 5' untranslated leader region and the IAPP coding region were sequenced by the dideoxy chain termination method of Sanger to ensure that no mutations were introduced.

To ensure that the transgene would be expressed in mouse cells, pRIPHAT I (SEQ ID NO: 1) was transiently transfected into βTC cells by means of electroporation as described by Mosselman et. al. ( FEBS Lett. 271, 33–36. 1990). Total RNA was isolated by established methods (Chomozynski and Sachi, Anal. Biochem. 162, 156–159) 24 hours later. The transgene-specific RNA was detected by PCR amplification of the cDNA derived from this total RNA by reverse transcription(Innis, M. A. et al. eds., PCR Protocols, Academic Press, New York 1990). The size and abundance of the PCR product demonstrated that the transgene was expressed and that the human albumin intron portion of the transgene was efficiently spliced out in these cells.

The Stably Transfected Cell Lines

The above described plasmids were stably introduced into RIN and βTC3 cells by electroporation along with a plasmid that confers geneticin(G418) resistance to the recipient cell. βTC3 cells were obtained from Shimon Efrat and Cold Spring Harbor Laboratory, Cold Spring Harbor, N.Y., and are described in Efrat, S. et al. Proc. Natl. Acad. Sci. 85, 9037–9041 (1988). Cells were prepared for electroporation by trypsinization of semi-confluent monolayers, pelleting twice, 1 wash in serum-free RPMI 1640 medium and resuspension in this medium at a concentration of $2 \times 10^7$ cells/ml. Routinely 50 µg of the appropriate plasmid along with 3.3 µg of the selection plasmid pHA2.3neo (confers G418 resistance; Dr. Peter Hobart, Pfizer, Inc.) were added to 0.5 ml of cells in a electroporation cuvette (Bethesda Research Labs [BRL], Gaithersburg, Md.) and subjected to 250 v/cm Field at 800 µF and low resistance setting on a BRL Cell-Porator electroporation unit. The cells were allowed to rest for 2 minutes. They were then diluted with 2 volumes of RPMI 1640 10% fetal bovine serum and transferred to T25 flasks. After 36 hrs, viable cells were transferred to 6 well cluster dishes and grown at a concentration of $2 \times 10^5$ cells in selection medium (same as above with 500 µg/ml active Geneticin). Colonies appeared after 3 weeks and they were isolated by established methods using trypsin and grease-coated porcelain cloning rings. Clones which survived this procedure were grown to mass culture, frozen and stored in liquid nitrogen. Confirmation of transgene expression was obtained by PCR amplification of cDNA derived from the clones' total RNA. In addition, a radioimmunoassay (Peninsula labs kit # RIK-7321, Belmont, Calif.) was performed on both total cell protein and surrounding medium to confirm both increased IAPP content and secretion.

Transgenic Mice.

Embryos from mouse strain FVB/N (Taketo, M. et al. Proc. Natl. Acad. Sci 88, 2065–2069 [1991]) were injected with linear DNA fragments that were isolated from the plasmid described above. The 2395 bp RIPHAT DNA fragment was released from its plasmid by cleavage with the Xba I and Xho I restriction endonucleases. The 2395 bp transgene fragment was isolated by electroelution (65V, 3 hrs.) after 2 rounds of agarose (0.9% GTG agarose, FMC Bioproducts, Rockland, Me) gel electrophoresis of the reaction digest. The fragment was further purified on a Schleicher and Schuell Elutip-d column following manufacturer's Elutip-d Basic Protocol for DNA purification prior to being injected into the embryos. Injection of the embryos was carried out according to published procedures, as outlined in Hogan, B. et al. Manipulating the Mouse Embryo Cold Spring Harbor Laboratories, New York, 1986.

Optimal Expression and Preferred Embodiments

Figure 1B:
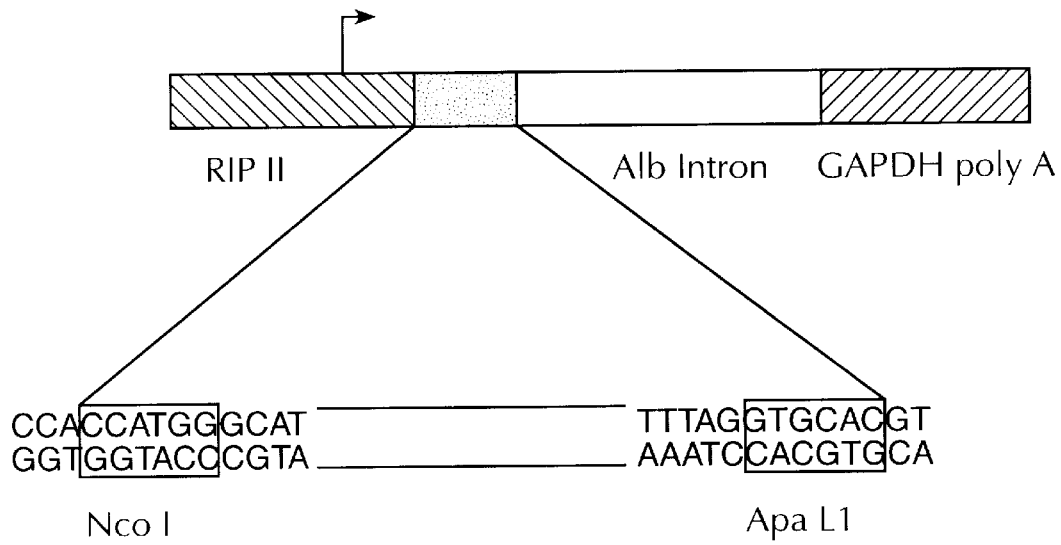
FIG. 1b is an enlargement of the ends of the coding region demonstrating the restriction sites that can be used to substitute alternative cDNAs for human IAPP.
Figure 1C:
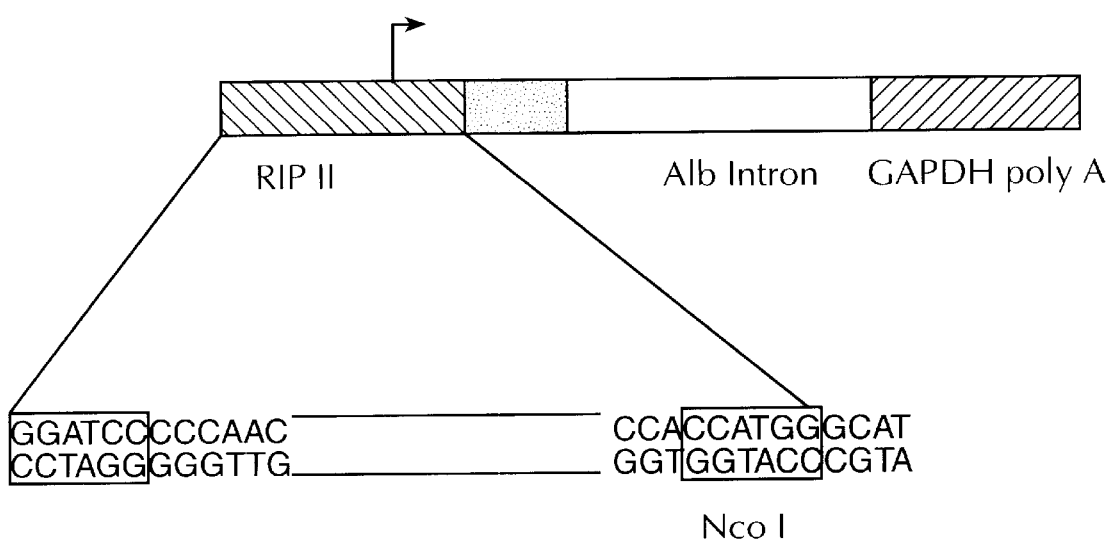
FIG. 1c is an enlargement of the ends of the promoter region demonstrating the restriction sites that can be used to substitute alternate promoters for RIP II in the RIPHAT transgene.

The plasmids as described above can be altered to optimize expression of the transgene such as various insertions, deletions and/or single or multiple base pair substitutions. This includes single base pair alterations in the region in front of the initiation codon of luciferase to optimize translational efficiency. The promoter region within pRIPHAT 1 can be exchanged for other promoters, such as human IAPP, rat insulin 1, mouse insulin, mouse IAPP, rat glucokinase (liver and/or β cell-specific), human gastrin, human or mouse albumin, mouse metallothionein and human tyrosine aminotransferase (FIG. 1b). The rat insulin II promoter is depicted as a darkly shaded box, the coding region as a black box, the human albumin intron as a white box and the human GAPDH polyadenylation region as a striped box. IAPP cDNAs of other species such as mouse, or mutated functional forms of human IAPP that retain either the amyloidogenic portions or the portions that induce insulin resistance, can be substituted for the human IAPP cDNA region within pRIPHAT1 (FIG. 1c). The transgene DNAs can be injected into other mouse strain embryos and mutants thereof, including db/+, Ob/+, $A^{uy}$ or $A^u$ on either a C57BL/6J or C57BL/Ks background. Alternatively, these transgenic mice can be mated to strains with these genetic traits.

The preferred cell lines include βTC3 (Cold Spring Harbor Laboratories), RINm5f (Gazdar, A. F. et al. PNAS 77, 3519–3523 [1980] obtained from W. Chick, U. Mass., Worcester, Mass.) and HIT (Santerre, R. F. et al. PNAS 78, 4339–4343 [1981]; obtained from ATCC Rockville Md.).

Utility

The stably transfected cell lines can be used to screen drugs for their ability to alter transcription, mRNA levels, translation, accumulation or secretion of human IAPP. In particular, steady state levels of transgene mRNA can be screened in a high throughput fashion using PCR detection methods. The cells can also be used to determine the mechanism of action of candidate drugs that are found to alter the above-mentioned processes.

The transgenic animals can be used to screen drugs for their ability to alter human IAPP levels in cells, tissues, organs and/or plasma. They can also be used to study the pathological consequences of human IAPP overexpression in whole animals.

Experimental

Materials and Methods

Restriction enzymes including ApaLI, Bam HI, Hind III, Nco, Not I, Xba I, Xho I and Eco RI were obtained from New England Biolabs. DNA modifying enzymes including T4 DNA Ligase and T4 DNA Kinase were obtained from the same source. Bacterial alkaline phosphatase was obtained from Boehringer Mannheim. All commercially obtained enzymes were utilized under conditions described as optimal by the supplier.

Media

The media for growth of *E. coli* consisted of 10 g Bacto-tryptone, 5 g Bacto-yeast extract and 5 g NaCl. The pH was adjusted to 7.5 with 10N NaOH after addition of all the ingredients.

Ethanol Precipitation of DNA

Sodium acetate(NaOAc) from a 3M, pH 5.2 stock solution was added to a DNA sample to bring the final NaOAc concentration to 200 mM. Two and one-half volumes of cold(−20° C.) absolute ethanol were added to the one volume of aqueous DNA sample and the sample placed at −70° C. for 15 min. or −20° C. overnight.

Electrophoresis of DNA

DNA in 10 mM Tris-HCl, pH 7.6 (or Hepes, pH 7.6), 1 mM EDTA was mixed with ⅕ volume of Loading buffer. Loading Buffer consisted of 30% glycerol, 10 mM Tris-HCl, pH 7.6, 20 mM ethylene diamine tetra acetic acid(EDTA), bromophenol blue. 0.25% (w/v)and xylene cyanol, 0.25% (w/v). DNA was electrophoresed through 0.8–1.2% (w/v) GTG agarose ( FMC Bioproducts, Rockland, Me.) at 5–10 volts per cm of distance between electrodes in 1×Tris-Borate EDTA (TBE) buffer (89 mM Tris, pH 8.3, 89 mM Borate, 2 mM EDTA).

Electroelution of DNA

DNA bands were removed from gels by cutting out a gel slice containing the band of interest with a clean single-edged razor blade and placing the gel slice in a 0.25 inch diameter dialysis tube (BRL Life Technologies, Inc., Gaithersburg, Md.)(length varying with size of gel slice) that was filled with 0.5×TBE buffer and subsequently sealed on both ends with dialysis tube clips. The filled tube was placed in a standard electrophoresis gel box filled with 0.5×TBE buffer and the DNA eluted out of the gel slice onto the inner side of the dialysis tube by applying a voltage of 10 volts/cm of distance between electrodes for 1–3 hours. At the end of this time the buffer solution containing the DNA was transferred to an eppendorf tube, concentrated in a Speed-Vac apparatus (Savant Instruments Inc. Farmingdale, N.Y.) to reduce the volume to a minimum of 100 μl. This volume was applied to a prepacked G-50 Sephadex (Pharmacia, Piscataway, N.J.) spin column and centrifuged for 3 min. at 600 G force.in an IEC tabletop clinical centrifuge (International Equipment Company, Needham HTS, Mass.). This allowed removal of the borate salt from the DNA sample. The sample was then ethanol precipitated and resuspended in 10 mM Tris, pH 7.6 and 1 mM EDTA.

Visualization of DNA Bands in Gels

For DNA to be electrophoresed through agarose gels, ¹⁄₁₀ volume of a 1 mg/ml ethidium bromide (EtBr) solution was added to the sample. DNA bands were visualized after electrophoresis by placing the gel on a UV transilluminator emitting UV light at a wavelength of 320 nm. By this method no destaining procedure was required. DNA bands in gel slices isolated for preparative purposes were electroeluted as described above. The EtBr bound to the DNA was removed by the ethanol precipitation procedure.

Preparation of Bacterial Plasmid DNA

Maxiprep Procedure (for yields of 100 to 2000 μgs of plasmid DNA).

This DNA was prepared by the alkaline lysis procedure described in Maniatis, Molecular Cloning: A Laboratory Manual. 0.5 liters of Luria broth, described under "Media" was inoculated with a 0.1 ml volume of a stationary phase culture of the appropriate *E. coli* strain. After adding 125 μg of dry ampicillin powder to the inoculated media, the bacteria were incubated at 37° C. with shaking overnight. The next morning the bacteria were pelleted by centrifugation in a Sorvall GS3 rotor (Dupont Instrument Products, Biomedical Division, Newton, Conn.) at 5,000 rpm for 10 min at 4° C. The pelleted bacteria were resuspended in 20 ml of a solution consisting of 50 mM glucose, 25 mM Tris-HCl, pH 8.0, 10 mM EDTA and 5 mg/ml lysozyme. The bacteria were left at room temperature for 10 minutes, after which time 40 ml of 0.2 M NaOH/1% SDS was added. The lysed bacteria were allowed to sit at room temperature for an additional 10 minutes after which time we added 20 ml of ice cold 3 M sodium acetate, pH 5.2, and the mixture incubated on ice for 10 min. The white precipitate was pelleted by centrifugation in the original tubes for 10 min. at 5,000 rpm in the GS3 rotor. The supernatant was collected and the volume measured. The DNA was precipitated by addition of one equal volume of isopropanol and pelleted by centrifugation in a Sorvall HSA rotor at 7,500 rpm for 15 minutes at 4° C. The pellet was dissolved in 2 ml of 10 mM Tris-HCl and added to a 5 ml polystyrene tube containing 3.10 gm of CsCl. The sample was transferred to a 3.9 ml Beckman heat seal tube containing 50 μl of a 10 mg/ml solution of EtBr, filled with water, placed in a Beckmann TLN 100 rotor and centrifuged for 4 hours at 100,000 rpm.in an Optima TLX Beckman tabletop Ultracentrifuge (Beckman Instruments, Palo Alto, Calif.). Bands of plasmid DNA were visible to the naked eye and extracted with a 20 G needle and 1 cc tuberculin syringe. The EtBr was removed by extracting the plasmid solution with 3 M NaCl-saturated isopropanol. The DNA was subsequently ethanol-precipitated and stored at −20° C.

Miniprep Procedure(for yields of 1 to 20 μgs of plasmid DNA)

This DNA was prepared by the boiling water procedure described in Maniatis, Molecular Cloning: A Laboratory Manual. 1.5 ml of a stationary culture of *E. coli* was poured into a 1.5 ml eppendorf tube. The remainder of the culture was stored at 4° C. The tube was centrifuged at 12,000 G for 15 seconds in an Eppendorf microfuge at room temperature. The supernatant was removed by aspiration and the pellet resuspended in 0.4 ml of STET buffer: 8% sucrose, 0.5% Triton X100 detergent, 50 mM EDTA, 50 mM Tris-HCl, pH 8.0. 35 pl of 10 mg/ml of lysozyme was added to the resuspended cells. The tube was immediately placed in 100° C. water for 1 minute. The tube was removed from the boiling water and centrifuged for 15 minutes at 12,000 G.

200 ul of the supernatant was transferred to a new tube and mixed with 200 μl of isopropanol. The sample was stored at −70° C. for 15 minutes after which time the precipitated DNA was recovered by centrifugation at 12,000 G at 4° C. for 10 minutes. The DNA pellet was rinsed with 70% ethanol and allowed to air dry. The pellet was resuspended in 50 μl of 10 mM Tris-HCl. pH 7.6, 1 mM EDTA and stored at 4° C.

Oral Glucose Tolerance Test

Mice to be tested were fasted for >12 hours; blood samples were obtained from retro-orbital eye bleeds; blood glucose determinations were carried out by use of a "One Touch" Glucometer (Lifescan Inc., Milpitas Calif.). Blood sampling was carried out before administration of a glucose challenge(t=0), and 30, 75 and 120 minutes after glucose challenge. The glucose challenge consisted of a 200 mg/ml dextrose solution administered orally at a 1 mg/gm body weight dose by means of a 1 cc syringe and murine oral dosing needle.

Bacterial plasmid DNA was prepared by the alkaline lysis method described in Maniatis, Molecular Cloning: A Laboratory Manual.

E. coli Transformation.

The bacterial strains consisted of either SURE cells obtained from Stratagene, Inc. or DH5 cells from Bethesda Research Labs, Gaithersburg, Md. Competent cells were prepared according to the $CaCl_2$ method (Maniatis et al. Molecular Cloning, Cold Spring Harbor Laboratories, 2nd Ed. 1989), flash frozen in liquid nitrogen and stored at −70° C. Transformation of these strains with plasmids of interest were typically carried out by incubation of 10 ul of ligation mix with 80 ul of competent cells followed by heat shock at 37° C. for 2 min and subsequent incubation at 37° C. for 1 hr after addition of 0.8 ml Luria broth. Typically, 100 ul of this mixture was plated on LB plates containing 50 ug/ml ampicillin as the selection agent. Colonies were picked after overnight incubation of the plate at 37° C.

EXAMPLE 1

Construction of pRIPHAT

Construction of pSV2Dog15

A DNA fragment containing the human glyceraldehyde-3-phosphate dehydrogenase polyadenylation/ transcriptional termination region (SEQ ID NO: 5) was generated by polymerase chain reaction( PCR) amplification. The oligonucleotides 18970.244 (SEQ ID NO: 11) and 18970.246 (SEQ ID NO: 10) were incubated with 3 ug of human genomic DNA (Clontech, San Carlos, Calif.) under standard PCR conditions: 1 uM primers, 3 ug target DNA, 200 uM dNTPs, 2.5 units Amplitaq DNA polymerase, 10 mM Tris-HCl, pH 8.3, 50 mM KCl, 1.5mM $MgCl_2$. The amplification conditions were set at 25 cycles, 1 min at 96° C., 2 min at 58° C., 3 min at 72° C. The resulting 545 bp fragment was digested with 10 units of Spe I and 10 units of Bam HI (37° C./30 min) and ligated to 1 ug of phosphatased, SpeI/Bam-digested vector DNA pSV2dog1 to generate plasmid pSV2dog11. pSV2Dog11 itself was then digested with Spe I and treated with alkaline phospahatase (0.25 units from Boehringer Mannheim, in 50 mM TrisHCl, pH 8.5 at 55° C. for 2 hours). A DNA fragment containing the human albumin intron I (SEQ ID NO: 3) was generated by PCR amplification of 3 ug of human genomic DNA (Clontech) utilizing oligonucleotides 18505.022 and 18505.024 under standard conditions described above. The resulting 740 bp fragment was digested with Spe I and ligated to Spe I-linearized pSV2 Dog11 under standard ligation conditions to generate plasmid pSV2Dog15. The orientation of the intron fragment was confirmed by digestion of pSV2Dog15 with restriction endonuclease Aat 1. 20 ug of pSV2Dog15 was digested with 60 units of Bam HI and 22.5 units of Nco I to isolate a Nco I/BamH I fragment by electroelution. Three micrograms of this fragment was subsequently digested with 20 units of Apa LI for 4 hrs. at 37° C. The resulting digestion products were separated on a 0.8% GTG agarose (FMC Bioproducts, Rockland, Me.) gel. A 1265 bp Bam HI/Apa LI fragment was recovered by electroelution (standard conditions: 60 V/60 minutes in 0.5×TBE(Tris-borate-EDTA pH 8.3) with the gel slice in a dialysis bag). The eluted DNA was purified by spin column chromatography using G50 resin followed by ethanol precipitation. This fragment contained the human albumin intron fused on its 3' end to the human GAPDH polyadenylation region.

Construction of pSLA10

A portion of the human IAPP cDNA (SEQ ID NO: 2) containing only the protein coding region of the IAPP message was generated by PCR. Oligonucleotides 19383.288 (SEQ ID NO: 12) and 19383.292 (SEQ ID NO: 15), at a concentration of 1 uM were incubated with 0.1 ng cloned IAPP cDNA Hsiapp1 (Mosselman et al.) as the template. Standard buffer and cycling conditions, as described above, were utilized. The reaction products were extracted with chloroform to remove residual mineral oil and ethanol precipitated. The precipitated DNA was resuspended in 20 ul of 1×NEB 4 restriction endonuclease buffer and 10 units of restriction endonuclease Apa LI. The digestion products were electrophoresed in a 1% GTG agarose gel, visualized by ethidium bromide staining, and recovered by electroelution with a yield of 1.1 ug. This fragment was ligated to the BamHI/Apa LI, 1265 bp fragment from pSV2Dog15 in a total volume of 20 ul in 1×BRL ligation buffer plus units T4 DNA Ligase. The reaction was incubated at 16° C. for 3 days. The residual ligase activity present in this reaction after this incubation was heat-inactivated (65° C./10 min.). This ligation reaction was then diluted to 100 ul in the presence of high salt restriction buffer (100 mM NaCl, 10 mm Tris, pH 7.6, 10 mM $MgCl_2$) and digested with 5 units of Nco I for 2 hrs. at 37° C. The resultant fragment (1533 bp) was isolated by electrophoresis followed by electroelution.

The shuttle vector for cloning this fragment was prepared by digestion of 20 ug of the reporter plasmid pSuperluc (pSL) with 9 units of Nco I and 20 units of Bam HI at 37° C. for 3 hrs. in a reaction volume of 100 ul. To this reaction, 5 ul of 1M Tris, pH 8.0 and 22 units of alkaline phosphatase were added. The reaction was now allowed to proceed at 50° C. for 2 hrs. to remove phosphate groups on the 5' overhangs and thus prevent recircularization of the vector alone in subsequent ligation steps. The phosphatase reaction was terminated by phenol/chloroform extraction followed by ethanol precipitation. The DNA was resuspended in 10 mM Hepes, pH 7.6, 1 mM EDTA (HE) at a concentration of 0.2 ug/ul.

The 1533 bp IAPP cDNA/albumin intron/GAPDH polyA fragment was cloned into Nco I/Bam HI-cut pSL by ligation of 1.1 ug of the insert to 0.2 ug of the pSL vector in a volume of 20 ul in 1×BRL ligation buffer and 400 units of T4 DNA Ligase. The reaction was incubated at 16° C. overnight. On the following morning, competent E. coli SURE cells (Stratagene, San Diego, Calif.) were incubated with 10 ul of ligation mix at 0° C. for 20 min followed by a 2 min heat shock at 37° C. 0.8 ml of Luria Broth were added to the mix and incubated at 37° C. for 60 min. 100 ul of this mix were spread onto a Luria Broth Agar plate containing 200 ug/ml ampicillin. Sixteen ampicillin-resistant colonies were picked and cultured in liquid broth; half of these cultures harbored plasmids with the proper insert as determined by digestion of miniprep DNAs (as described in Materials and Methods). One culture (miniprep #3) was grown up to 0.5 liter in Luria Broth for a NDA maxiprep and its plasmid was designated pSLA10.

Construction of pSLA11

The next step involved the insertion of the rat insulin II promoter (RIP) (SEQ ID NO: 2) into pSLA10. Because RIP contains an internal Nco I site, this process was carried out in 2 stages. The RIP DNA fragment itself (876 bp: 700 bp of 5' flank plus 176 bp of 5' untranslated leader including the first intron) was synthesized by PCR under standard conditions (above) utilizing 1 uM each of oligonucleotides 19383.284 (SEQ ID NO: 14) and 19383.292 (SEQ ID NO: 15); 3 ug of rat genomic DNA (Clontech) was used as the template. Oligonucleotide 19383.292 contains a single base alteration (A to C) 2 nucleotides 5' of the initiation codon in order to allow ligation of RIP to the IAPP coding region via a Nco I site. The PCR product was chloroform extracted and ethanol precipitated. The DNA was resuspended in 20 ul of 1×NEB (New England Biolabs) 4 restriction buffer along with 5 units of Nco I and incubated at 37° C. for 2 hrs. Two DNA fragments were recovered from this digestion by electrophoresis through 1.0% GTG agarose, visualization by ethidium bromide staining and electroetution of the DNA from the gel slices: a 708 bp DNA with 2 Nco I ends containing the transcriptional start site and 5' leader region and a 168 bp blunt end/Nco I fragment containing the 5' most flanking sequence of the rat insulin II promoter.

The plasmid pSLA10 was first cleaved with Xba I. Ten micrograms of pSLA10 was digested with 20 units of Xba I in a volume of 100 ul of 1×high salt restriction buffer (100 mM NaCl, 10 mM Tris, pH 7.6, 10 mM $MgCl_2$) for 2 hrs. at 37° C. The reaction was stopped by phenol/chloroform extraction followed by ethanol precipitation. The 5' single stranded DNA overhangs were filled in by a polymerization step: the DNA was resuspended in 10 ul of 10 mM Hepes, pH 7.6, 1 mM EDTA and added to a final reaction volume of 100 ul containing 10 mM Tris, pH 7.6, 10 mm $MgCl_2$, 50 mM NaCl, 5 units of Klenow enzyme and 25 uM dNTPs. This reaction was allowed to proceed at room temperature overnight. On the following morning, the fill-in reaction was heated at 65° C. for 10 min to inactivate the Klenow enzyme; afterwards 2 ul of 6M NaCl and 5 units of restriction endonuclease Nco I were added and the reaction allowed to proceed at 37° C. for 2 hrs. The cleavage reaction was stopped by the addition of 20 ul of gel loading buffer; consisting of 30% glycerol, 10 mM Tris-HCl, pH 7.6, 20 mM ethylene diamine tetra acetic acid (EDTA), bromophenol blue; 0.25% (w/v and xylene cyanol, 0.25% (w/v), the resulting mix was electrophoresed through a 0.8% GTG agarose gel. The linear form of the digested pSLA10 plasmid was recovered by electroelution followed by centrifugation through a G-50 spin column and ethanol precipitation. The precipitated DNA was resuspended in 10 ul of 10 mM Hepes, pH7.6, 1 mM EDTA. Two microliters (1 ug) of this solution was incubated with 0.25 ug of the 174 bp blunt end/Nco I fragment of the rat insulin promoter, 5 units of NEB T4 DNA ligase and 1×BRL (Bethesda Research Laboratories) ligation buffer in a final volume of 20 ul and incubated at 16° C. overnight. The next morning 10 ul of the ligation reaction were used to transform competent *E. coli* SURE cells. Miniprep DNA was prepared (as described in Materials and Methods) from cultures of 16 colonies; 2 displayed Bam HI fragments of the correct size. One of these clones was grown as a DNA maxiprep as described in the Materials and Methods for preparation of more plasmid DNA and given the designation pSLA11.

pSLA11 was incubated with 7.5 units of Nco I in a volume of 200 ul in 1×NEB4 buffer at 37° C. for 2 hrs. followed by the addition of 10 ul of 1 mM Tris pH 8.0 and 22 units of Boehringer Mannheim alkaline phosphatase and further incubation at 50° C. for 2 hrs. This was followed by 3 sequential phenol/chloroform extractions and ethanol precipitation. 0.32 ug of this linearized form of pSLA11 was ligated to 0.5 ug of the 760 bp Nco I rat insulin II promoter fragment described above in a volume of 20 ul in 1×BRL ligation buffer containing 20 units of NEB T4 DNA ligase; the reaction was incubated at 16° C. overnight. Ten microliters of this ligation reaction were used to transform competent *E. coli* SURE cells (as described in Maniatis, Molecular Cloning: A Laboratory Manual). Of 8 colonies that arose from this transformation event, one miniprep DNA preparation displayed the correctly sized bands as determined by comparison to DNA molecular weight markers supplied by Bethesda Research Laboratories, Bethesda, Md., when digested with restriction endonuclease Eco RI. This plasmid was partially digested with Bam HI and the transgene insert, 2.4 kb in length, was ligated to Bam HI-digested Bluescript SK(−); generating pRIPHAT (SEQ. ID NO: 1)) in order to facilitate DNA sequence determination. One of 5 independently derived clones displayed no inappropriate mutations and was used to prepare transgene insert for microinjection.

Preparation of RIPHAT DNA for Microinjection

Three hundred micrograms of pRIPHAT (SEQ. ID NO: 1) were digested with 300 units each of restriction endonucleases Xba I and Xho I in a total reaction volume of 600 ul at 37° C. for 2 hrs. The reaction was stopped by the addition of EDTA to a concentration of 21 mM, followed by the addition of loading buffer and 2 rounds of electrophoresis through a 0.5% GTG agarose gel. The gel slice containing the 2.4 kb DNA fragment was removed and the DNA isolated by electroelution (65V, 3 hrs.). The RIPHAT transgene fragment (2.4 kb (SEQ. ID. NO: 7)) was further purified utilizing a Schleicher and Schuell Elutip-d column and following the manufacturers protocol. The yield was 5.6 ug of purified RIPHAT fragment. pRIPHAT1 was deposited with the American Type Culture Collection on Apr. 27, 1995 and received the designation ATCC 69794. This DNA was delivered to the Pfizer transgenic facility for microinjection.

Microinjection of Mouse Embryos and Generation of Transgenic Mice

The microinjection of mouse embryos and generation of transgenic mice was carried out by published procedures. Detailed procedures describing the preparation of mice, the microinjection procedure, the reimplantation of injected embryos, the maintenance of foster mothers, and the recovery and maintenance of transgenic lines can be found in Gordon, J and Ruddle, F., Methods in Enzymology 101, 411–433 (1983). Embryos were isolated from female F1 progeny of strain FVB/N inbred crosses. The actual injection procedure was carried out as described in Wagner, T. et al. PNAS 78, 6376–6380 (1981) except that injected eggs were transferred immediately to donor females instead of 5 day incubations in culture tubes. Mice resulting from the reimplantation events were tested for presence of the transgene in their genomic DNA by slot/Southern blotting of DNA isolated from tail biopsies. Those testing positive were crossed to nontransgenic FVB/N mice of the opposite sex. Offspring of these crosses were tested for transmission of the transgene by obtaining tail biopsies, isolating genomic DNA from them and PCR amplifying transgene sequences using primers 22018–134–1 (5'-CGAGTGGGCTATGGGTTTGT-3') (SEQ ID NO: 16) and 22018–134-2 (5'-GTCATGTGCACCTAAAGGGGCAAGTAATTCA-3') (SEQ ID NO: 17) to generate a diagnostic 883 bp PCR DNA product.

Establishment of Transgenic Lines

Those offspring testing positive for presence of the transgene were backcrossed to FVB/N mice for establishment of transgenic lines. Injection of 280 FVB/N embryos resulted in generation of 10 RIPHAT founders. Six of these founders were able to transmit the transgene to their offspring, as determined by PCR amplification of transgene sequences from genomic DNA isolated from offspring tail biopsies.

Identification of Lines Expressing the Transgene

Total RNA was prepared from various tissues of offspring from the 6 lines (including pancreas, liver and kidney). The RNA was isolated by polytron (Brinkmann Instruments, Westbury, N.Y.) homogenization of each of the tissues in 2 ml of TRISOLV™ (Biotecx Laboratories, Houston, Tex.) denaturant for 60 seconds. Addition of 4 ml of chloroform allowed separation of the homogenate into an upper, aqueous phase and a lower phenol/chloroform phase. The RNA was precipitated by addition of an equal volume of isopropanol to the aqueous phase of each homogenate. The isopropanol precipitates were centrifuged at 12,000 G for 10 min at 4° C., washed once with 75% ethanol and allowed to air dry. The RNA samples were resuspended in 200 μl of 1 mM EDTA and their concentration determined by UV spectrophotometry. Northern analysis was carried out as described in Maniatis, utilizing 1.0% GTG formaldehyde agarose gels, blotting to Nylon membranes and hybridizing the blot to a $32^P$-labelled DNA fragment that corresponds to the human GAPDH polyadenylation region within the RIPHAT transgene. RIPHAT-specific RNA was detected in lines RHA, RHF and RHC, with lines RHA and RHF displaying 10 fold higher pancreatic expression than line RHC. Line RHF was selected for colony expansion.

Generation of Line RHF Homozygotes

The transgenic hemizygous RHF offspring were subjected to brother-sister matings to generate nontransgenic to hemizygote to homozygote offspring in a 1:2:1 ratio. Transgenic offspring were identified by PCR analysis of tail biopsies; homozygotes within this group were identified by test-crossing the transgenics to wild-type FVB/N mates and identifying those animals that would generate no nontransgenic offspring (>20 offspring per putative homozygote). Homozygotes that were identified in this manner were intercrossed to generate a colony of RHF homozygotes.

Determination of Plasma IAPP and Insulin Levels

Representative nontransgenic littermates, hemizygous and homozygous animals were sacrificed by $CO_2$ asphyxiation. Whole blood was obtained from Vena Cava puncture of asphyxiated animals with a 20G needle and 1 ml tuberculin syringe. The whole blood was transferred to 1.0 ml Microtainer Plasma separator tubes (Becton Dickinson, Rutherford, N.J.) to prevent coagulation and centrifuged at 2000 G for 2 min to allow plasma isolation. The plasmas were quick frozen in dry ice and stored at −70° C. until assayed.

Use of Line RHF Homozygotes for Drug Screening

Typically, animals are divided into groups of 10 for each dose of a given test compound. Their plasma glucose levels are determined by retro-orbital eye bleeds on day 1 before dosing. Dosing is carried out daily, e.g., at 0.1, 1.0 and 10 mg/kg, for days 1 through 4. On day 5 the animals are bled to determine their fasting plasma glucose levels with the aim of detecting a glucose lowering effect. Alternatively, the animals are subjected to an oral glucose tolerance test (OGTT) to demonstrate improved glucose tolerance. The animals are then exsanguinated in order to measure plasma insulin levels and demonstrate a drop in insulin concentration.

---

What is claimed is:

1. A transgenic mouse whose somatic and germ cells contain a recombinant DNA sequence comprising in operable linkage, a rat insulin II promoter, a sequence encoding the human IAPP, a human albumin intron I sequence, a human GAPDH termination sequence and a human GAPDH polyadenylation sequence, wherein the expression of said recombinant DNA sequence results in a diabetic phenotype of fasting hyperglycemia.

2. The transgenic mouse according to claim 1, wherein said sequence encoding the human IAPP is genomic DNA.

3. The transgenic mouse according to claim 1, wherein said sequence encoding the human IAPP is cDNA.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 5356 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:1:

```
CTGACGCGCC CTGTAGCGGC GCATTAAGCG CGGCGGGTGT GGTGGTTACG CGCAGCGTGA      60

CCGCTACACT TGCCAGCGCC CTAGCGCCCG CTCCTTTCGC TTTCTTCCCT TCCTTTCTCG     120

CCACGTTCGC CGGCTTTCCC CGTCAAGCTC TAAATCGGGG GCTCCCTTTA GGGTTCCGAT     180

TTAGTGCTTT ACGGCACCTC GACCCCAAAA AACTTGATTA GGGTGATGGT TCACGTAGTG     240

GGCCATCGCC CTGATAGACG GTTTTTCGCC CTTTGACGTT GGAGTCCACG TTCTTTAATA     300

GTGGACTCTT GTTCCAAACT GGAACAACAC TCAACCCTAT CTCGGTCTAT TCTTTTGATT     360

TATAAGGGAT TTTGCCGATT TCGGCCTATT GGTTAAAAAA TGAGCTGATT TAACAAAAAT     420

TTAACGCGAA TTTTAACAAA ATATTAACGC TTACAATTTC CATTCGCCAT TCAGGCTGCG     480
```

```
CAACTGTTGG GAAGGGCGAT CGGTGCGGGC CTCTTCGCTA TTACGCCAGC TGGCGAAAGG    540

GGGATGTGCT GCAAGGCGAT TAAGTTGGGT AACGCCAGGG TTTTCCCAGT CACGACGTTG    600

TAAAACGACG GCCAGTGAGC GCGCGTAATA CGACTCACTA TAGGGCGAAT TGGGTACCGG    660

GCCCCCCCTC GAGGTCGACG GTATCGATAA GCTTGATATC GAATTCCTGC AGCCCGGGGG    720

ATCCCCCAAC CACTCCAAGT GGAGGCTGAG AAAGGTTTTG TAGCTGGGTA GAGTATGTAC    780

TAAGAGATGG AGACAGCTGG CTCTGAGCTC TGAAGCAAGC ACCTCTTATG GAGAGTTGCT    840

GACCTTCAGG TGCAAATCTA AGATACTACA GGAGAATACA CCATGGGCT  TCAGCCCAGT    900

TGACTCCCGA GTGGGCTATG GGTTTGTGGA AGGAGAGATA GAAGAGAAGG GACCTTTCTT    960

CTTGAATTCT GCTTTCCTTC TACCTCTGAG GGTGAGCTGG GGTCTCAGCT GAGGTGAGGA   1020

CACAGCTATC AGTGGGAACT GTGAAACAAC AGTTCAAGGG ACAAAGTTAC TAGGTCCCCC   1080

AACAACTGCA GCCTCCTGGG GAATGATGTG GAAAAATGCT CAGCCAAGGA CAAAGAAGGC   1140

CTCACCCTCT CTGAGACAAT GTCCCCTGCT GTGAACTGGT TCATCAGGCC ACCCAGGAGC   1200

CCCTATTAAG ACTCTAATTA CCCTAAGGCT AAGTAGAGGT GTTGTTGTCC AATGAGCACT   1260

TTCTGCAGAC CTAGCACCAG GCAAGTGTTT GGAAACTGCA GCTTCAGCCC CTCTGGCCAT   1320

CTGCTGATCC ACCCTTAATG GGACAAACAG CAAAGTCCAG GGGTCAGGGG GGGTGCTTT    1380

GGACTATAAA GCTAGTGGGG ATTCAGTAAC CCCCAGCCCT AAGTGACCAG CTACAGTCGG   1440

AAACCATCAG CAAGCAGGTA TGTACTCTCC AGGGTGGGCC TGGCTTCCCC AGTCAAGACT   1500

CCAGGGATTT GAGGGACGCT GTGGGCTCTT CTCTTACATG TACCTTTTGC TAGCCTCAAC   1560

CCTGACTATC TTCCAGGTCA TTGTTCCACC ATGGGCATCC TGAAGCTGCA AGTATTTCTC   1620

ATTGTGCTCT CTGTTGCATT GAACCATCTG AAAGCTACAC CCATTGAAAG TCATCAGGTG   1680

GAAAAGCGGA AATGCAACAC TGCCACATGT GCAACGCAGC GCCTGGCAAA TTTTTTAGTT   1740

CATTCCAGCA ACAACTTTGG TGCCATTCTC TCATCTACCA ACGTGGGATC CAATACATAT   1800

GGCAAGAGGA ATGCAGTAGA GGTTTTAAAG AGAGAGCCAC TGAATTACTT GCCCCTTTAG   1860

GTGCACGTAA GAAATCCATT TTTCTATTGT TCAACTTTTA TTCTATTTTC CCAGTAAAAT   1920

AAAGTTTTAG TAAACTCTGC ATCTTTAAAG AATTATTTTG GCATTTATTT CTAAAATGGC   1980

ATAGCATTTT GTATTTGTGA AGTCTTACAA GGTTATCTTA TTAATAAAAT TCAAACATCC   2040

TAGGTAAAAA AAAAAGGTCA GAATTGTTTA GTGACTGTAA TTTTCTTTTG CGCACTAAGG   2100

AAAGTGCAAA GTAACTTAGA GTGACTGAAA CTTCACAGAA TAGGGTTGAA GATTGAATTC   2160

ATAACTATCC CAAAGACCTA TCCATTGCAC TATGCTTTAT TTAAAAACCA CAAAACCTGT   2220

GCTGTTGATC TCATAAATAG AACTTGTATT TATATTTATT TACATTTTAG TCTGTCTTCT   2280

TGGTTGCTGT TGATAGACAC TAAAAGAGTA TTAGATATTA TCTAAGTTTG AATATAAGGC   2340

TATAAATATT TAATAATTTT TAAAATAGTA TTCTTGGTAA TTGAATTATT CTTCTGTTTA   2400

AAGGCAGAAG AAATAATTGA ACATCATCCT GAGTTTTTCT GTAGGAATCA GAGCCCAATA   2460

TTTTGAAACA AATGCATAAT CTAAGTCAAA TGGAAAGAAA TATAAAAAGT AACATTATTA   2520

CTTCTTGTTT TCTTCAGTAT TTAACAATCC TTTTTTTTCT TCCCTTGCCC AGACAAGCTT   2580

CTAGTGACCC CTGGACCACC AGCCCCAGCA AGAGCACAAG AGGAAGAGAG AGACCCTCAC   2640

TGCTGGGGAG TCCCTGCCAC ACTCAGTCCC CCACCACACT GAATCTCCCC TCCTCACAGT   2700

TGCCATGTAG ACCCCCTGAA GAGGGGAGGG GCCTAGGGAG CCGCACCTTG TCATGTACCA   2760

TCAATAAAGT ACCCTGTGCT CAACCAGTTA CTTGTCCTGT CTTATTCTAG GGTCTGGGGC   2820

AGAGGGGAGG GAAGCTGGGC TTGTGTCAAG GTGAGACATT CTTGCTGGGG AGGGACCTGG   2880
```

```
TATGTTCTCC TCAGACTGAG GGTAGGGCCT CCAAACAGCC TTGCTTGCTT CGAGAACCAT    2940

TTGCTTCCCG CTCAGACGTC TTGAGTGCTA CAGGAAGCTG GCACCACTAC TTCAGAGAAC    3000

AAGGCCTTTT CCTCTCCTCG CTCCAGTCCT AGGCTATCTG CTGTTGGCCA AACATGGAAG    3060

AAGCTATTCT GTGGGCAGCT CCAGGGAGGC TGACAGGTGG AGGAAGTCAG GGCGGATCCA    3120

CTAGTTCTAG AGCGGCCGCC ACCGCGGTGG AGCTCCAGCT TTTGTTCCCT TTAGTGAGGG    3180

TTAATTGCGC GCTTGGCGTA ATCATGGTCA TAGCTGTTTC CTGTGTGAAA TTGTTATCCG    3240

CTCACAATTC CACACAACAT ACGAGCCGGA AGCATAAAGT GTAAAGCCTG GGGTGCCTAA    3300

TGAGTGAGCT AACTCACATT AATTGCGTTG CGCTCACTGC CCGCTTTCCA GTCGGGAAAC    3360

CTGTCGTGCC AGCTGCATTA ATGAATCGGC CAACGCGCGG GGAGAGGCGG TTTGCGTATT    3420

GGGCGCTCTT CCGCTTCCTC GCTCACTGAC TCGCTGCGCT CGGTCGTTCG GCTGCGGCGA    3480

GCGGTATCAG CTCACTCAAA GGCGGTAATA CGGTTATCCA CAGAATCAGG GGATAACGCA    3540

GGAAAGAACA TGTGAGCAAA AGGCCAGCAA AAGGCCAGGA ACCGTAAAAA GGCCGCGTTG    3600

CTGGCGTTTT TCCATAGGCT CCGCCCCCCT GACGAGCATC ACAAAAATCG ACGCTCAAGT    3660

CAGAGGTGGC GAAACCCGAC AGGACTATAA AGATACCAGG CGTTTCCCCC TGGAAGCTCC    3720

CTCGTGCGCT CTCCTGTTCC GACCCTGCCG CTTACCGGAT ACCTGTCCGC CTTTCTCCCT    3780

TCGGGAAGCG TGGCGCTTTC TCATAGCTCA CGCTGTAGGT ATCTCAGTTC GGTGTAGGTC    3840

GTTCGCTCCA AGCTGGGCTG TGTGCACGAA CCCCCCGTTC AGCCCGACCG CTGCGCCTTA    3900

TCCGGTAACT ATCGTCTTGA GTCCAACCCG GTAAGACACG ACTTATCGCC ACTGGCAGCA    3960

GCCACTGGTA ACAGGATTAG CAGAGCGAGG TATGTAGGCG GTGCTACAGA GTTCTTGAAG    4020

TGGTGGCCTA ACTACGGCTA CACTAGAAGG ACAGTATTTG GTATCTGCGC TCTGCTGAAG    4080

CCAGTTACCT TCGGAAAAAG AGTTGGTAGC TCTTGATCCG GCAAACAAAC CACCGCTGGT    4140

AGCGGTGGTT TTTTGTTTG CAAGCAGCAG ATTACGCGCA GAAAAAAAGG ATCTCAAGAA    4200

GATCCTTTGA TCTTTTCTAC GGGGTCTGAC GCTCAGTGGA ACGAAAACTC ACGTTAAGGG    4260

ATTTTGGTCA TGAGATTATC AAAAAGGATC TTCACCTAGA TCCTTTTAAA TTAAAAATGA    4320

AGTTTTAAAT CAATCTAAAG TATATATGAG TAAACTTGGT CTGACAGTTA CCAATGCTTA    4380

ATCAGTGAGG CACCTATCTC AGCGATCTGT CTATTTCGTT CATCCATAGT TGCCTGACTC    4440

CCCGTCGTGT AGATAACTAC GATACGGGAG GGCTTACCAT CTGGCCCCAG TGCTGCAATG    4500

ATACCGCGAG ACCCACGCTC ACCGGCTCCA GATTTATCAG CAATAAACCA GCCAGCCGGA    4560

AGGGCCGAGC GCAGAAGTGG TCCTGCAACT TTATCCGCCT CCATCCAGTC TATTAATTGT    4620

TGCCGGGAAG CTAGAGTAAG TAGTTCGCCA GTTAATAGTT TGCGCAACGT TGTTGCCATT    4680

GCTACAGGCA TCGTGGTGTC ACGCTCGTCG TTTGGTATGG CTTCATTCAG CTCCGGTTCC    4740

CAACGATCAA GGCGAGTTAC ATGATCCCCC ATGTTGTGCA AAAAAGCGGT TAGCTCCTTC    4800

GGTCCTCCGA TCGTTGTCAG AAGTAAGTTG GCCGCAGTGT TATCACTCAT GGTTATGGCA    4860

GCACTGCATA ATTCTCTTAC TGTCATGCCA TCCGTAAGAT GCTTTTCTGT GACTGGTGAG    4920

TACTCAACCA AGTCATTCTG AGAATAGTGT ATGCGGCGAC CGAGTTGCTC TTGCCCGGCG    4980

TCAATACGGG ATAATACCGC GCCACATAGC AGAACTTTAA AAGTGCTCAT CATTGGAAAA    5040

CGTTCTTCGG GGCGAAAACT CTCAAGGATC TTACCGCTGT TGAGATCCAG TTCGATGTAA    5100

CCCACTCGTG CACCCAACTG ATCTTCAGCA TCTTTTACTT TCACCAGCGT TTCTGGGTGA    5160

GCAAAAACAG GAAGGCAAAA TGCCGCAAAA AAGGGAATAA GGGCGACACG GAAATGTTGA    5220
```

| ATACTCATAC TCTTCCTTTT TCAATATTAT TGAAGCATTT ATCAGGGTTA TTGTCTCATG | 5280 |
| AGCGGATACA TATTTGAATG TATTTAGAAA AATAAACAAA TAGGGGTTCC GCGCACATTT | 5340 |
| CCCCGAAAAG TGCCAC | 5356 |

(2) INFORMATION FOR SEQ ID NO:2:

(i) SEQUENCE CHARACTERISTICS:
        (A) LENGTH: 876 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

| GGATCCCCCA ACCACTCCAA GTGGAGGCTG AGAAAGGTTT TGTAGCTGGG TAGAGTATGT | 60 |
| ACTAAGAGAT GGAGACAGCT GGCTCTGAGC TCTGAAGCAA GCACCTCTTA TGGAGAGTTG | 120 |
| CTGACCTTCA GGTGCAAATC TAAGATACTA CAGGAGAATA CACCATGGGG CTTCAGCCCA | 180 |
| GTTGACTCCC GAGTGGGCTA TGGGTTTGTG GAAGGAGAGA TAGAAGAGAA GGGACCTTTC | 240 |
| TTCTTGAATT CTGCTTTCCT TCTACCTCTG AGGGTGAGCT GGGGTCTCAG CTGAGGTGAG | 300 |
| GACACAGCTA TCAGTGGGAA CTGTGAAACA ACAGTTCAAG GGACAAAGTT ACTAGGTCCC | 360 |
| CCAACAACTG CAGCCTCCTG GGAATGATG TGGAAAAATG CTCAGCCAAG GACAAAGAAG | 420 |
| GCCTCACCCT CTCTGAGACA ATGTCCCCTG CTGTGAACTG GTTCATCAGG CCACCCAGGA | 480 |
| GCCCCTATTA AGACTCTAAT TACCCTAAGG CTAAGTAGAG GTGTTGTTGT CCAATGAGCA | 540 |
| CTTTCTGCAG ACCTAGCACC AGGCAAGTGT TTGGAAACTG CAGCTTCAGC CCCTCTGGCC | 600 |
| ATCTGCTGAT CCACCCTTAA TGGGACAAAC AGCAAAGTCC AGGGGTCAGG GGGGGGTGCT | 660 |
| TTGGACTATA AAGCTAGTGG GGATTCAGTA ACCCCCAGCC CTAAGTGACC AGCTACAGTC | 720 |
| GGAAACCATC AGCAAGCAGG TATGTACTCT CCAGGGTGGG CCTGGCTTCC CCAGTCAAGA | 780 |
| CTCCAGGGAT TTGAGGGACG CTGTGGGCTC TTCTCTTACA TGTACCTTTT GCTAGCCTCA | 840 |
| ACCCTGACTA TCTTCCAGGT CATTGTTCCA CCATGG | 876 |

(2) INFORMATION FOR SEQ ID NO:3:

(i) SEQUENCE CHARACTERISTICS:
        (A) LENGTH: 278 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

| CCATGGGCAT CCTGAAGCTG CAAGTATTTC TCATTGTGCT CTCTGTTGCA TTGAACCATC | 60 |
| TGAAAGCTAC ACCCATTGAA AGTCATCAGG TGGAAAAGCG GAAATGCAAC ACTGCCACAT | 120 |
| GTGCAACGCA GCGCCTGGCA AATTTTTTAG TTCATTCCAG CAACAACTTT GGTGCCATTC | 180 |
| TCTCATCTAC CAACGTGGGA TCCAATACAT ATGGCAAGAG GAATGCAGTA GAGGTTTTAA | 240 |
| AGAGAGAGCC ACTGAATTAC TTGCCCCTTT AGGTGCAC | 278 |

(2) INFORMATION FOR SEQ ID NO:4:

(i) SEQUENCE CHARACTERISTICS:
        (A) LENGTH: 720 base pairs
        (B) TYPE: nucleic acid
        (C) STRANDEDNESS: double (D) TOPOLOGY: linear (ii) MOLECULE TYPE: DNA (genomic)

(xi) SEQUENCE DESCRIPTION: SEQ ID NO:4:

| | | | | | |
|---|---|---|---|---|---|
| GTGCACGTAA | GAAATCCATT | TTTCTATTGT | TCAACTTTTA | TTCTATTTTC | CCAGTAAAAT | 60 |
| AAAGTTTTAG | TAAACTCTGC | ATCTTTAAAG | AATTATTTTG | GCATTTATTT | CTAAAATGGC | 120 |
| ATAGCATTTT | GTATTTGTGA | AGTCTTACAA | GGTTATCTTA | TTAATAAAAT | TCAAACATCC | 180 |
| TAGGTAAAAA | AAAAAGGTCA | GAATTGTTTA | GTGACTGTAA | TTTTCTTTTG | CGCACTAAGG | 240 |
| AAAGTGCAAA | GTAACTTAGA | GTGACTGAAA | CTTCACAGAA | TAGGGTTGAA | GATTGAATTC | 300 |
| ATAACTATCC | CAAAGACCTA | TCCATTGCAC | TATGCTTTAT | TTAAAAACCA | CAAAACCTGT | 360 |
| GCTGTTGATC | TCATAAATAG | AACTTGTATT | TATATTTATT | TACATTTTAG | TCTGTCTTCT | 420 |
| TGGTTGCTGT | TGATAGACAC | TAAAAGAGTA | TTAGATATTA | TCTAAGTTTG | AATATAAGGC | 480 |
| TATAAATATT | TAATAATTTT | TAAAATAGTA | TTCTTGGTAA | TTGAATTATT | CTTCTGTTTA | 540 |
| AAGGCAGAAG | AAATAATTGA | ACATCATCCT | GAGTTTTTCT | GTAGGAATCA | GAGCCCAATA | 600 |
| TTTTGAAACA | AATGCATAAT | CTAAGTCAAA | TGGAAAGAAA | TATAAAAAGT | AACATTATTA | 660 |
| CTTCTTGTTT | TCTTCAGTAT | TTAACAATCC | TTTTTTTTCT | TCCCTTGCCC | AGACAAGCTT | 720 |

(2) INFORMATION FOR SEQ ID NO:5:

(i) SEQUENCE CHARACTERISTICS:
        (A) LENGTH: 545 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

| | | | | | |
|---|---|---|---|---|---|
| AAGCTTCTAG | TGACCCCTGG | ACCACCAGCC | CCAGCAAGAG | CACAAGAGGA | AGAGAGAGAC | 60 |
| CCTCACTGCT | GGGGAGTCCC | TGCCACACTC | AGTCCCCCAC | CACACTGAAT | CTCCCCTCCT | 120 |
| CACAGTTGCC | ATGTAGACCC | CCTGAAGAGG | GGAGGGGCCT | AGGGAGCCGC | ACCTTGTCAT | 180 |
| GTACCATCAA | TAAAGTACCC | TGTGCTCAAC | CAGTTACTTG | TCCTGTCTTA | TTCTAGGGTC | 240 |
| TGGGGCAGAG | GGGAGGGAAG | CTGGGCTTGT | GTCAAGGTGA | GACATTCTTG | CTGGGGAGGG | 300 |
| ACCTGGTATG | TTCTCCTCAG | ACTGAGGGTA | GGGCCTCCAA | ACAGCCTTGC | TTGCTTCGAG | 360 |
| AACCATTTGC | TTCCCGCTCA | GACGTCTTGA | GTGCTACAGG | AAGCTGGCAC | CACTACTTCA | 420 |
| GAGAACAAGG | CCTTTTCCTC | TCCTCGCTCC | AGTCCTAGGC | TATCTGCTGT | TGGCCAAACA | 480 |
| TGGAAGAAGC | TATTCTGTGG | GCAGCTCCAG | GGAGGCTGAC | AGGTGGAGGA | AGTCAGGGCG | 540 |
| GATCC | | | | | | 545 |

(2) INFORMATION FOR SEQ ID NO:6:

(i) SEQUENCE CHARACTERISTICS:
        (A) LENGTH: 2961 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:6:

| | | | | | |
|---|---|---|---|---|---|
| CTGACGCGCC | CTGTAGCGGC | GCATTAAGCG | CGGCGGGTGT | GGTGGTTACG | CGCAGCGTGA | 60 |
| CCGCTACACT | TGCCAGCGCC | CTAGCGCCCG | CTCCTTTCGC | TTTCTTCCCT | TCCTTTCTCG | 120 |

-continued

```
CCACGTTCGC CGGCTTTCCC CGTCAAGCTC TAAATCGGGG GCTCCCTTTA GGGTTCCGAT      180

TTAGTGCTTT ACGGCACCTC GACCCCAAAA AACTTGATTA GGGTGATGGT TCACGTAGTG      240

GGCCATCGCC CTGATAGACG GTTTTTCGCC CTTTGACGTT GGAGTCCACG TTCTTTAATA      300

GTGGACTCTT GTTCCAAACT GGAACAACAC TCAACCCTAT CTCGGTCTAT TCTTTTGATT      360

TATAAGGGAT TTTGCCGATT TCGGCCTATT GGTTAAAAAA TGAGCTGATT TAACAAAAAT      420

TTAACGCGAA TTTTAACAAA ATATTAACGC TTACAATTTC CATTCGCCAT TCAGGCTGCG      480

CAACTGTTGG GAAGGGCGAT CGGTGCGGGC CTCTTCGCTA TTACGCCAGC TGGCGAAAGG      540

GGGATGTGCT GCAAGGCGAT TAAGTTGGGT AACGCCAGGG TTTTCCCAGT CACGACGTTG      600

TAAAACGACG GCCAGTGAGC GCGCGTAATA CGACTCACTA TAGGGCGAAT TGGGTACCGG      660

GCCCCCCCTC GAGGTCGACG GTATCGATAA GCTTGATATC GAATTCCTGC AGCCCGGGGG      720

ATCCACTAGT TCTAGAGCGG CCGCCACCGC GGTGGAGCTC CAGCTTTTGT TCCCTTTAGT      780

GAGGGTTAAT TGCGCGCTTG GCGTAATCAT GGTCATAGCT GTTTCCTGTG TGAAATTGTT      840

ATCCGCTCAC AATTCCACAC AACATACGAG CCGGAAGCAT AAAGTGTAAA GCCTGGGGTG      900

CCTAATGAGT GAGCTAACTC ACATTAATTG CGTTGCGCTC ACTGCCCGCT TTCCAGTCGG      960

GAAACCTGTC GTGCCAGCTG CATTAATGAA TCGGCCAACG CGCGGGGAGA GGCGGTTTGC     1020

GTATTGGGCG CTCTTCCGCT TCCTCGCTCA CTGACTCGCT GCGCTCGGTC GTTCGGCTGC     1080

GGCGAGCGGT ATCAGCTCAC TCAAAGGCGG TAATACGGTT ATCCACAGAA TCAGGGGATA     1140

ACGCAGGAAA GAACATGTGA GCAAAAGGCC AGCAAAAGGC CAGGAACCGT AAAAAGGCCG     1200

CGTTGCTGGC GTTTTTCCAT AGGCTCCGCC CCCCTGACGA GCATCACAAA AATCGACGCT     1260

CAAGTCAGAG GTGGCGAAAC CCGACAGGAC TATAAAGATA CCAGGCGTTT CCCCCTGGAA     1320

GCTCCCTCGT GCGCTCTCCT GTTCCGACCC TGCCGCTTAC CGGATACCTG TCCGCCTTTC     1380

TCCCTTCGGG AAGCGTGGCG CTTTCTCATA GCTCACGCTG TAGGTATCTC AGTTCGGTGT     1440

AGGTCGTTCG CTCCAAGCTG GGCTGTGTGC ACGAACCCCC CGTTCAGCCC GACCGCTGCG     1500

CCTTATCCGG TAACTATCGT CTTGAGTCCA ACCCGGTAAG ACACGACTTA TCGCCACTGG     1560

CAGCAGCCAC TGGTAACAGG ATTAGCAGAG CGAGGTATGT AGGCGGTGCT ACAGAGTTCT     1620

TGAAGTGGTG GCCTAACTAC GGCTACACTA GAAGGACAGT ATTTGGTATC TGCGCTCTGC     1680

TGAAGCCAGT TACCTTCGGA AAAAGAGTTG GTAGCTCTTG ATCCGGCAAA CAAACCACCG     1740

CTGGTAGCGG TGGTTTTTTT GTTTGCAAGC AGCAGATTAC GCGCAGAAAA AAAGGATCTC     1800

AAGAAGATCC TTTGATCTTT TCTACGGGGT CTGACGCTCA GTGGAACGAA AACTCACGTT     1860

AAGGGATTTT GGTCATGAGA TTATCAAAAA GGATCTTCAC CTAGATCCTT TTAAATTAAA     1920

AATGAAGTTT TAAATCAATC TAAAGTATAT ATGAGTAAAC TTGGTCTGAC AGTTACCAAT     1980

GCTTAATCAG TGAGGCACCT ATCTCAGCGA TCTGTCTATT TCGTTCATCC ATAGTTGCCT     2040

GACTCCCCGT CGTGTAGATA ACTACGATAC GGGAGGGCTT ACCATCTGGC CCCAGTGCTG     2100

CAATGATACC GCGAGACCCA CGCTCACCGG CTCCAGATTT ATCAGCAATA AACCAGCCAG     2160

CCGGAAGGGC CGAGCGCAGA AGTGGTCCTG CAACTTTATC CGCCTCCATC CAGTCTATTA     2220

ATTGTTGCCG GGAAGCTAGA GTAAGTAGTT CGCCAGTTAA TAGTTTGCGC AACGTTGTTG     2280

CCATTGCTAC AGGCATCGTG GTGTCACGCT CGTCGTTTGG TATGGCTTCA TTCAGCTCCG     2340

GTTCCCAACG ATCAAGGCGA GTTACATGAT CCCCCATGTT GTGCAAAAAA GCGGTTAGCT     2400

CCTTCGGTCC TCCGATCGTT GTCAGAAGTA AGTTGGCCGC AGTGTTATCA CTCATGGTTA     2460
```

```
TGGCAGCACT GCATAATTCT CTTACTGTCA TGCCATCCGT AAGATGCTTT TCTGTGACTG    2520

GTGAGTACTC AACCAAGTCA TTCTGAGAAT AGTGTATGCG GCGACCGAGT TGCTCTTGCC    2580

CGGCGTCAAT ACGGGATAAT ACCGCGCCAC ATAGCAGAAC TTTAAAAGTG CTCATCATTG    2640

GAAAACGTTC TTCGGGGCGA AAACTCTCAA GGATCTTACC GCTGTTGAGA TCCAGTTCGA    2700

TGTAACCCAC TCGTGCACCC AACTGATCTT CAGCATCTTT TACTTTCACC AGCGTTTCTG    2760

GGTGAGCAAA AACAGGAAGG CAAAATGCCG CAAAAAAGGG AATAAGGGCG ACACGGAAAT    2820

GTTGAATACT CATACTCTTC CTTTTTCAAT ATTATTGAAG CATTTATCAG GGTTATTGTC    2880

TCATGAGCGG ATACATATTT GAATGTATTT AGAAAAATAA ACAAATAGGG GTTCCGCGCA    2940

CATTTCCCCG AAAAGTGCCA C                                              2961

(2) INFORMATION FOR SEQ ID NO:7:

(i) SEQUENCE CHARACTERISTICS:
        (A) LENGTH: 2395 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

GATCCCCCAA CCACTCCAAG TGGAGGCTGA GAAAGGTTTT GTAGCTGGGT AGAGTATGTA      60

CTAAGAGATG GAGACAGCTG GCTCTGAGCT CTGAAGCAAG CACCTCTTAT GGAGAGTTGC     120

TGACCTTCAG GTGCAAATCT AAGATACTAC AGGAGAATAC ACCATGGGGC TTCAGCCCAG     180

TTGACTCCCG AGTGGGCTAT GGGTTTGTGG AAGGAGAGAT AGAAGAGAAG GGACCTTTCT     240

TCTTGAATTC TGCTTTCCTT CTACCTCTGA GGGTGAGCTG GGGTCTCAGC TGAGGTGAGG     300

ACACAGCTAT CAGTGGGAAC TGTGAAACAA CAGTTCAAGG GACAAAGTTA CTAGGTCCCC     360

CAACAACTGC AGCCTCCTGG GGAATGATGT GGAAAAATGC TCAGCCAAGG ACAAAGAAGG     420

CCTCACCCTC TCTGAGACAA TGTCCCCTGC TGTGAACTGG TTCATCAGGC CACCCAGGAG     480

CCCCTATTAA GACTCTAATT ACCCTAAGGC TAAGTAGAGG TGTTGTTGTC CAATGAGCAC     540

TTTCTGCAGA CCTAGCACCA GGCAAGTGTT TGGAAACTGC AGCTTCAGCC CCTCTGGCCA     600

TCTGCTGATC CACCCTTAAT GGGACAAACA GCAAAGTCCA GGGGTCAGGG GGGGGTGCTT     660

TGGACTATAA AGCTAGTGGG GATTCAGTAA CCCCCAGCCC TAAGTGACCA GCTACAGTCG     720

GAAACCATCA GCAAGCAGGT ATGTACTCTC CAGGGTGGGC CTGGCTTCCC CAGTCAAGAC     780

TCCAGGGATT TGAGGGACGC TGTGGGCTCT TCTCTTACAT GTACCTTTTG CTAGCCTCAA     840

CCCTGACTAT CTTCCAGGTC ATTGTTCCAC CATGGGCATC CTGAAGCTGC AAGTATTTCT     900

CATTGTGCTC TCTGTTGCAT TGAACCATCT GAAAGCTACA CCCATTGAAA GTCATCAGGT     960

GGAAAAGCGG AAATGCAACA CTGCCACATG TGCAACGCAG CGCCTGGCAA ATTTTTTAGT    1020

TCATTCCAGC AACAACTTTG GTGCCATTCT CTCATCTACC AACGTGGGAT CCAATACATA    1080

TGGCAAGAGG AATGCAGTAG AGGTTTTAAA GAGAGAGCCA CTGAATTACT TGCCCCTTTA    1140

GGTGCACGTA AGAAATCCAT TTTTCTATTG TTCAACTTTT ATTCTATTTT CCCAGTAAAA    1200

TAAAGTTTTA GTAAACTCTG CATCTTTAAA GAATTATTTT GGCATTTATT TCTAAAATGG    1260

CATAGCATTT TGTATTTGTG AAGTCTTACA AGGTTATCTT ATTAATAAAA TTCAAACATC    1320

CTAGGTAAAA AAAAAAGGTC AGAATTGTTT AGTGACTGTA ATTTTCTTTT GCGCACTAAG    1380

GAAAGTGCAA AGTAACTTAG AGTGACTGAA ACTTCACAGA ATAGGGTTGA AGATTGAATT    1440
```

```
CATAACTATC CCAAAGACCT ATCCATTGCA CTATGCTTTA TTTAAAAACC ACAAAACCTG    1500

TGCTGTTGAT CTCATAAATA GAACTTGTAT TTATATTTAT TTACATTTTA GTCTGTCTTC    1560

TTGGTTGCTG TTGATAGACA CTAAAAGAGT ATTAGATATT ATCTAAGTTT GAATATAAGG    1620

CTATAAATAT TTAATAATTT TTAAAATAGT ATTCTTGGTA ATTGAATTAT TCTTCTGTTT    1680

AAAGGCAGAA GAAATAATTG AACATCATCC TGAGTTTTTC TGTAGGAATC AGAGCCCAAT    1740

ATTTTGAAAC AAATGCATAA TCTAAGTCAA ATGGAAAGAA ATATAAAAAG TAACATTATT    1800

ACTTCTTGTT TTCTTCAGTA TTTAACAATC CTTTTTTTTC TTCCCTTGCC CAGACAAGCT    1860

TCTAGTGACC CCTGGACCAC CAGCCCCAGC AAGAGCACAA GAGGAAGAGA GAGACCCTCA    1920

CTGCTGGGGA GTCCCTGCCA CACTCAGTCC CCCACCACAC TGAATCTCCC CTCCTCACAG    1980

TTGCCATGTA GACCCCCTGA AGAGGGGAGG GGCCTAGGGA GCCGCACCTT GTCATGTACC    2040

ATCAATAAAG TACCCTGTGC TCAACCAGTT ACTTGTCCTG TCTTATTCTA GGGTCTGGGG    2100

CAGAGGGGAG GGAAGCTGGG CTTGTGTCAA GGTGAGACAT TCTTGCTGGG GAGGGACCTG    2160

GTATGTTCTC CTCAGACTGA GGGTAGGGCC TCCAAACAGC CTTGCTTGCT TCGAGAACCA    2220

TTTGCTTCCC GCTCAGACGT CTTGAGTGCT ACAGGAAGCT GGCACCACTA CTTCAGAGAA    2280

CAAGGCCTTT TCCTCTCCTC GCTCCAGTCC TAGGCTATCT GCTGTTGGCC AAACATGGAA    2340

GAAGCTATTC TGTGGGCAGC TCCAGGGAGG CTGACAGGTG GAGGAAGTCA GGGCG         2395

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCCTCTAGAA GCTTGTCTGG GCAAGGGAAG AAAA                                 34

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGGAAGCTTC TAGACTTTCG TCGAGGTGCA CGTAAGAA                             38

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CAAACCGGAT CCGCCCTGAC TTCCTCCACC TGTCAGC                              37

(2) INFORMATION FOR SEQ ID NO:11:
```

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CACAACACTA GTGACCCCTG GACCACCAGC CCCAGC                                    36

(2) INFORMATION FOR SEQ ID NO:12:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

GTCATGTGCA CCTAAAGGGG CAAGTAATTC A                                         31

(2) INFORMATION FOR SEQ ID NO:13:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:13:

GAAGCCATGG GCATCCTGAA GCTGCAAGTA                                           30

(2) INFORMATION FOR SEQ ID NO:14:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

GTCAGGAATT CGGATCCCCC AACCACTCCA AGT                                       33

(2) INFORMATION FOR SEQ ID NO:15:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

ACAGGGCCAT GGTGGAACAA TGACCTGGAA GATA                                      34